(12) United States Patent
Swamy

(10) Patent No.: US 8,853,188 B2
(45) Date of Patent: Oct. 7, 2014

(54) COMPOSITIONS AND METHODS FOR CANCER TREATMENT

(75) Inventor: Narasimha Swamy, Providence, RI (US)

(73) Assignee: Women and Infants Hospital of RI, Inc., Providence, RI (US)

( * ) Notice: Subject to any disclaimer, the term of this patent is extended or adjusted under 35 U.S.C. 154(b) by 0 days.

(21) Appl. No.: 13/402,023

(22) Filed: Feb. 22, 2012

(65) Prior Publication Data

US 2012/0270839 A1    Oct. 25, 2012

Related U.S. Application Data

(63) Continuation of application No. 11/885,606, filed as application No. PCT/US2006/007710 on Mar. 3, 2006, now abandoned.

(60) Provisional application No. 60/658,627, filed on Mar. 4, 2005.

(51) Int. Cl.
| | | |
|---|---|---|
| A61K 31/593 | (2006.01) | |
| A61K 31/695 | (2006.01) | |
| C07C 401/00 | (2006.01) | |
| A61K 31/59 | (2006.01) | |

(52) U.S. Cl.
CPC .................................... *A61K 31/59* (2013.01)
USPC ......................................... 514/167; 552/653

(58) Field of Classification Search
USPC ......................................... 514/167; 552/653
See application file for complete search history.

(56) References Cited

U.S. PATENT DOCUMENTS

| | | |
|---|---|---|
| 6,521,608 B1 | 2/2003 | Henner et al. |
| 6,787,660 B1 * | 9/2004 | Armbruster et al. .......... 552/653 |
| 6,929,797 B2 * | 8/2005 | Mazess et al. ............ 424/195.11 |
| 6,939,868 B2 | 9/2005 | DeLuca et al. |
| 8,133,694 B2 * | 3/2012 | Armbruster et al. ......... 435/7.93 |
| 2005/0059640 A1 * | 3/2005 | Bonner et al. ................. 514/154 |
| 2005/0059641 A1 | 3/2005 | Ray et al. |
| 2008/0317870 A1 | 12/2008 | Ray et al. |
| 2010/0113378 A1 | 5/2010 | Ray et al. |

FOREIGN PATENT DOCUMENTS

WO    2006/096555 A1    9/2006

OTHER PUBLICATIONS

Swamy et al. (AN 1996:533141 CAPLUS, DN 125:242199, abstract, Archives of Biochemistry and Biophysics (1996), 333(1), 139-144).*
Van Auken et al. (AN 1996:692233, DN 126:15121, original Nos. 126:30771,3080a abstract of Journal of Cellular Biohemisty (1996), 63(3),302-310).*
Ray, Rahul et al. (AN 1994:674731, CAPLUS,DN 121:274731, original reference No. 121:50015a, 50018a, abstract of Bioorganic Chemistry (1994), 22(3), 276-83).*
Van Auken et al. (Journal of Cellular Biohemisty (1996), 63(3),302-310).*
Ming L. Chen et al. (Archives of Biochemistry and Biophysics, vol. 370, No. 1, Oct. 1,pp. 34-44, 1999).*
Van Auken et al. (AN1996:692233 HCAPLUS, abstract of J. of Cellular BioChemistry, (1996, 63(3), 302-310).
Dorwald F.A. Side Reactions in Organic Synthesis, 2005, Wiley: VCH, Weinheim p. IX of Preface.
Gershell, L.J. et al. Nat. Rev. Drug Discovery 2003, 2 pp. 321-327.
Reed, J.C. et al., Nat. Rev. Drug Discovery 2002, 1, pp. 111-121.
Saijo, N. et al. Cancer Chemother. Pharmacol., 2003, 52, Suppl. 1: S97-101.

* cited by examiner

*Primary Examiner* — Sabiha N Qazi
(74) *Attorney, Agent, or Firm* — Saul Ewing, LLP; Peter C. Lauro, Esq.

(57) ABSTRACT

Bromoacetoxycalcidiol (B3CD), which is structurally related to calcidiol, exhibits cytotoxic and apoptotic activity toward cancer cells, including highly aggressive neuroblastoma cells. A series of small molecules designed around the structure of B3CD is expected to have growth inhibitory and apoptogenic activities toward a wide range of malignancies. B3CD shows no apparent toxicity in vivo, indicating potential value as a chemotherapeutic agent which will be particularly useful in treating highly aggressive tumors.

10 Claims, 14 Drawing Sheets

FIG. 6A                    FIG. 6B

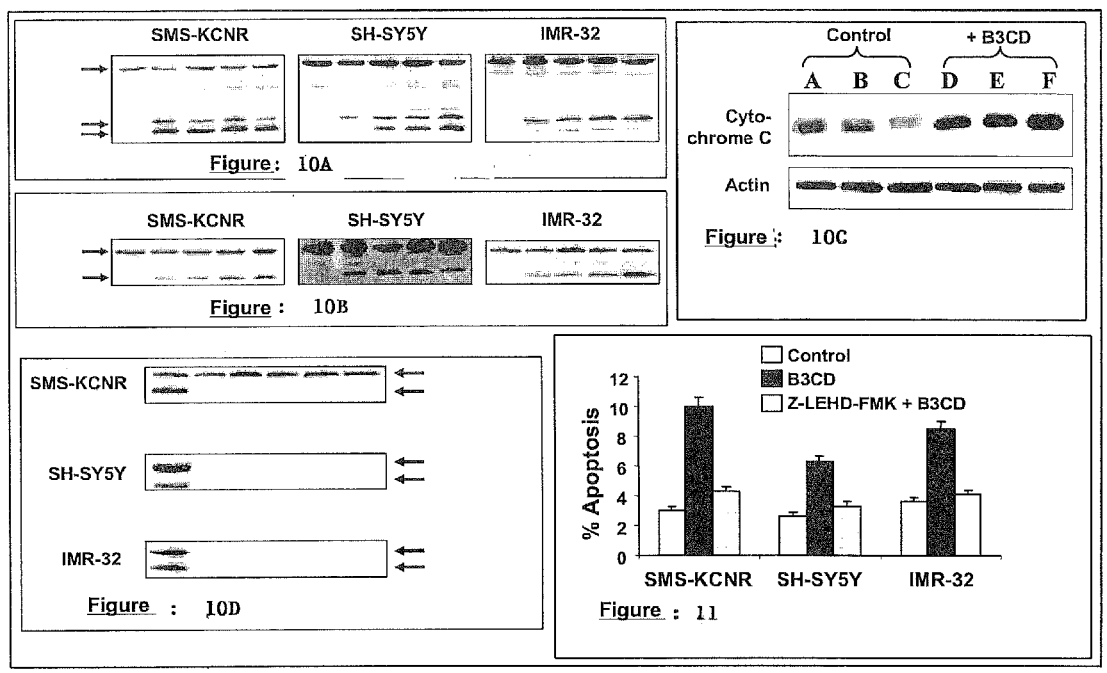

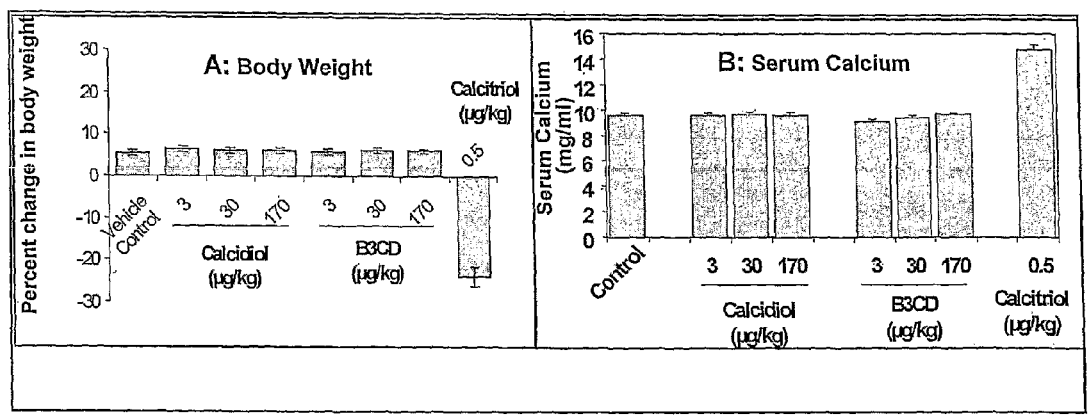
FIG. 15AFIG. 15B

COMPOSITIONS AND METHODS FOR CANCER TREATMENT

RELATED APPLICATIONS

This application is a continuation of U.S. application Ser. No. 11/885,606, filed Nov. 30, 2009, pending, which is the U.S. national phase application, pursuant to 35 U.S.C. §371, of PCT international application Ser. No. PCT/US2006/007710, filed Mar. 3, 2006, which claims priority to U.S. provisional application Ser. No. 60/658,627, filed Mar. 4, 2005. The entire contents of the aforementioned patent applications are incorporated herein in their entirety by this reference.

BACKGROUND OF THE INVENTION

1. Field of the Invention

The invention relates generally to the field of cancer chemotherapy and particularly to biologically active calcidiol derivatives for cancer cell inhibition.

2. Description of Background Art

Cancer is the second most common disease and also one of the most feared. Cancer occurs when cells continue to divide and fail to die at the appropriate time. Under normal circumstances, cells grow and divide to produce more cells as needed in order to maintain a healthy body. Tumors may form when this orderly process is disrupted by changes in regulatory processes that control normal cell growth and death, resulting in uncontrolled cell growth. Cancer may be induced by genetic changes, external factors such as diet, exposure to ultraviolet or other types of ionizing radiation, viruses, exposure to chemical carcinogens. In some cases, inherited genetic alterations may be a factor in development of cancer.

Regardless of which particular combination of factors contribute to the root cause of cancer, cumulative mutations may cause cancer cells to proliferate more rapidly than neighboring normal cells. Cell abnormalities passed down to cellular descendants may develop into clonal armies that continue to grow unabated. The cells may eventually develop the capacity through additional mutations to invade and destroy surrounding tissue. Thus, malignant cancers usually become life-threatening because they develop the power to disable the regulatory mechanisms that confine them to the specific tissue in which they arise. They subsequently disengage from the malignant tumor and travel through the bloodstream or lymphatic system where they eventually interfere with vital systems.

Novel therapeutic agents inhibiting tumor growth either directly or by impacting the tumor microenvironment are being developed and tested (Gershell L J, Atkins J H. A brief history of novel drug discovery technologies. *Nat Rev Drug Discov.* 2003; 2:321-327.) They include new classes of cytotoxic agents stimulating apoptosis, inhibiting angiogenesis and metastasis or alter tumor cell signaling pathways (Reed J C. Apoptosis-based therapies. *Nat Rev Drug Discov.* 2002; 1:111-121.) These new agents suppress tumor growth through multiple mechanisms. While core scaffolds have been used successfully in the past, (Tan D S. Current Progress in Natural Product-like Libraries for Discovery Screening Combinatorial Chemistry & High Throughput Screening, 2004; 7: 631-643) new compounds are necessary to advance the drug development efforts.

Neuroblastoma is a solid cancerous tumor that begins in nerve tissue in the /neck, chest, abdomen or pelvis but usually originates in the abdomen in adrenal gland tissue. By the time it is diagnosed, the cancer has usually metastasized to the lymph nodes, liver, lungs, bones and bone marrow.

Neuroblastoma (NB) is the most common heterogeneous and malignant tumor of early childhood. Two thirds of children with neuroblastoma are diagnosed when they are younger than 5 years. While frequently present at birth, neuroblastoma is usually not detected until later. In rare cases, neuroblastoma can be detected before birth by fetal ultrasound.

NB is the most common extracranial solid tumor in children. It is derived from the neural crest and is characterized by a marked clinical heterogeneity (aggressive, unremitting growth to spontaneous remission). Current treatment for high-risk patients includes surgery and high dose chemotherapy with autologous stem cell rescue. However, in spite of aggressive therapy, the disease relapses and up to 80% of patients die of disseminated disease. Eradication of refractory microscopic disease remains one of the most significant challenges in the treatment of high-risk neuroblastoma.

In a manner similar to other tumors, NB is known to produce endothelial growth factors that promote angiogenesis. Angiogenesis, the development of new blood vessels from the existing vasculature, is an essential component of solid tumor growth and metastasis. Several angiogenic factors are expressed by many tumors, suggesting that tumors promote their own vascularization by activating the host endothelium. Therefore, targeting angiogenesis is an attractive goal for targeting a variety of solid tumors including NB.

Treatment options for NB depend on age at diagnosis, tumor location, stage of the disease, regional lymph node involvement and the tumor biology. Generally four types of treatment are involved, alone or in combination, and include surgery to remove the tumor, radiation therapy, chemotherapy and bone marrow transplantation.

New and effective cancer treatments are constantly being sought. The most common therapies include radiation and drug treatments; unfortunately many are toxic and harmful to normal cells. Even when the majority of cells within a tumor are killed, a small number of unaffected cells may be able to reestablish the aberrant pattern of proliferation.

While most malignant cells appear at least initially to be highly susceptible to current cancer treatments, there is some speculation that subsets of cells are more resistant to drugs and radiation than normal, non-cancerous cells. Alternatively, tumor cells may simply develop resistance to chemical and radiation treatments, leading to recurrence of chemo- and/or radio-resistant cancers because the resistant cells maintain their ability to proliferate indefinitely. Resistance may also develop because administration of chemotherapeutic agents for the treatment of tumors is restricted by the toxicity of these agents to normal cells.

Deficiencies in the Art.

The severity of neuroblastoma is particularly disturbing. NB tumors grow aggressively, metastasize, induce angiogenesis and remain resistant to multimodal therapy, demonstrating the need for development of novel therapeutic strategies that address efficient inhibition of cancer cells and eradication of any remaining refractory microscopic disease.

There is an urgent need to improve the outcome for patients with this disease, with an increased emphasis for development of new drugs that are highly effective in eliminating aggressive cancer cells while also having insignificant toxicity toward normal cells.

Although state-of-the-art chemotherapy regimens have been established, the survival benefits still remain negligible (Saijo N, Tamura T, Nishio K. Strategy for the development of novel anticancer drugs. *Cancer Chemother Pharmacol.* 2003; 52 Suppl 1:S97-101). Therefore, effective new agents and innovative treatments are essential to fulfill this need. Intense and systematic research employing design and development of novel compounds along with in vitro and in vivo preclinical studies lead to the discovery of tumor specific agents that are useful as chemotherapeutic drugs. These novel agents may also lead to the identification of new molecular targets in cancer cells that can be furthered for drug development. Such discoveries create new frontiers for innovative cancer prevention and treatment strategies.

SUMMARY OF THE INVENTION

The present invention demonstrates the unexpected effect of a calcidiol derivative as an anti-angiogenic that inhibits cancer cell proliferation and promotes apoptosis of cancer cells. Bromoacetoxycalcidiol (B3CD) is inhibitory toward several types of cancer cells including breast, prostate and epithelial and is particularly effective against neuroblastoma. The compound shows no toxicity in murine models and has important potential as a chemotherapeutic agent in treatment of neuroblastoma as well as prostate cancers.

The discovery that B3CD is effective as a tumor inhibitor was prompted by the known activity of calcitriol (1,25-dihydroxy-vitamin D3), an endocrine hormone responsible for calcium and mineral homeostasis, in inhibiting cell proliferation and inducing differentiation. Numerous studies demonstrating that calcitriol is a potent inhibitor tumor growth provided the rationale for testing use of this secosteroid to treat leukemia, breast, prostate, colon, and skin cancers. Unfortunately, the clinical use of calcitriol was severely limited by its hypercalcemic side effects. Increased circulating levels of calcitriol were shown to elevate serum calcium to lethal levels (DeLuca H F, Zierold C. Mechanisms and functions of vitamin D. *Nutr Rev.* 1998; 56:S4-S10).

To combat unwanted side effects, a large number of synthetic analogs of calcitriol have been developed and used in animal models of various cancer types (Johannes P T M. Leeuwen V. Pols H A P. "Vitamin D: Anticancer and Differentiation," ed. by Feldman D., Glorieux F. H., Pike J. W., Academic Press, San Diego, pp. 1997; 1089-1105). However, the therapeutic efficacy of systemically applied calcitriol analogs for treating cancer remains hampered by lethal hypercalcemia at the supraphysiological doses needed to reach clinical improvement.

In contrast to calcitriol, calcidiol, a precursor to calcitriol, is largely biologically inactive and found abundantly in serum (approximately 1000 fold more; ~100 nM for calcidiol vs ~100 pM for calcitriol). Pharmacologic doses of calcidiol do not exhibit antiproliferative or antitumor activity. Therefore, as rationale in searching for cancer cell inhibitors, it was reasoned that calcidiol, which is a non calcemic precursor, could be used as a base structure to develop an effective chemotherapeutic drug, particularly in view of the fact that pharmacologic doses of calcidiol do not exhibit antiproliferative or antitumor activities (Kamao M, Tatematsu S, Hatakeyama S, Sakaki T, Sawada N, Inouye K, Ozono K, Kubodera N, Reddy G S, Okano T. C-3 epimerization of vitamin D3 metabolites and further metabolism of C-3 epimers: 25-hydroxyvitamin D3 is metabolized to 3-epi-25-hydroxyvitamin D3 and subsequently metabolized through C-1 alpha or C-24 hydroxylation. *J Biol Chem.* 2004; 279: 15897-15907). Since conversion of calcidiol to calcitriol by renal 1α-vitamin D-hydroxylase is under tight transcriptional control, an elevation in serum calcidiol level does not lead to an elevation of serum calcitriol or calcium levels. Consequently, calcidiol does not suffer from lethal calcemic side effects at supraphysiological doses.

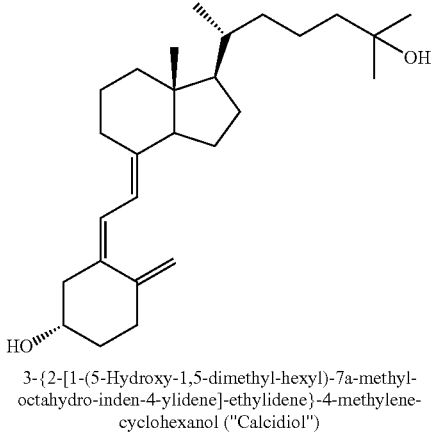 [SMILES: C=C1CC[C@H](O)C/C1=C/C=C1\CCC[C@@]2(C)C1CC[C@@H]2[C@H](C)CCCC(C)(C)O]

3-{2-[1-(5-Hydroxy-1,5-dimethyl-hexyl)-7a-methyl-octahydro-inden-4-ylidene]-ethylidene}-4-methylene-cyclohexanol ("Calcidiol")

(1 S,Z)-3-(2-((1R,7aR,E)-1-((R)-6-hydroxy-6-methylheptan-2-yl)-7a-methyloctahydro-4H-inden-4-ylidene)ethylidene)-4-methylenecyclohexan-1-ol ("Calcidiol")

Based on these considerations, calcidiol was modified at the 3-hydroxy position with 2-bromoacetic acid to synthesize the calcidiol derivative, B3CD (FIG. 1).

Other related B3CD compounds are contemplated to have similar activities and will be useful in developing panels or cocktails of related compounds with a range of related activities. Well-known procedures for chemical modifications will be used to modify B3CD (FIG. 1), replacing bromine, for example, with other halogens (F, Cl, I), $N_3$, N2, —$NH_2$, CN, S—$CH_3$, —N=C=S (see FIG. 2). The chain length between the A ring and the functionality can also be varied as well as various modifications between these groups and the A ring (see FIG. 3).

The side-chain modifications of the B3CD molecule shown in FIG. 4 are also contemplated.

A library of compounds based on the structure and activity of the lead compound, B3CD to probe for physiological activities such as cytotoxicity towards EC, PC and OC cells and angiogenesis as indicated will be synthesized. Preliminary studies indicate that the C-3 monobromoacetic acid ester (bromoacetoxy) derivative (1) of calcidiol (25-hydroxyvitamin $D_3$) exhibits cytotoxicity. A small number of additional related compounds, including isotopically labeled analogs, have been prepared and these are also shown. The isotopically labeled derivatives are not separately depicted. A significant number of ester derivatives at the 3-hydroxyl position of calcidiol will be synthesized. These leads will be utilized in the screening the cell lines.

5
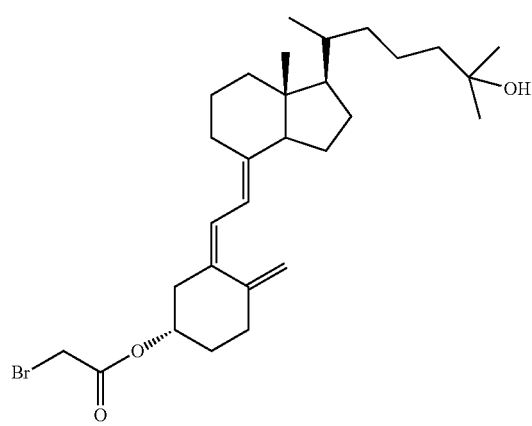
(1)
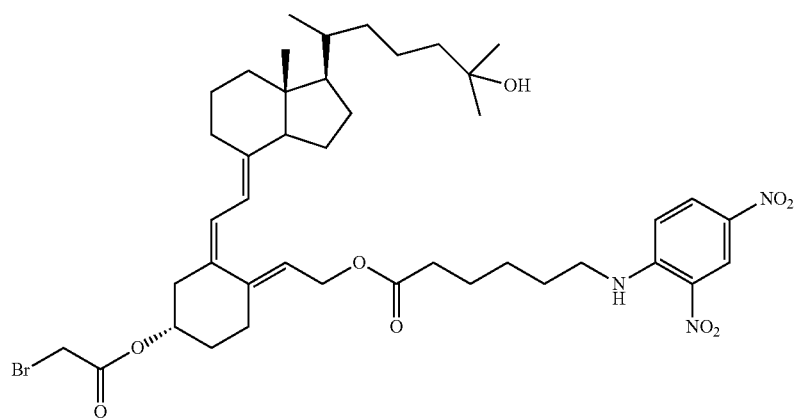
6
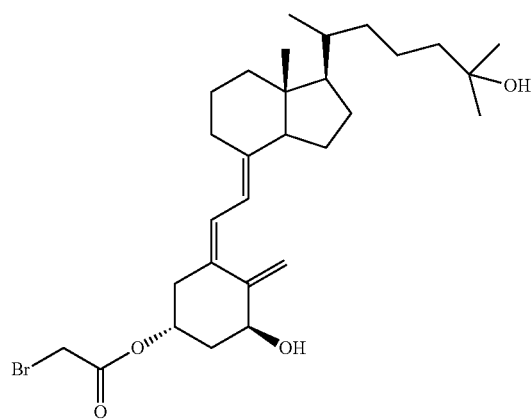
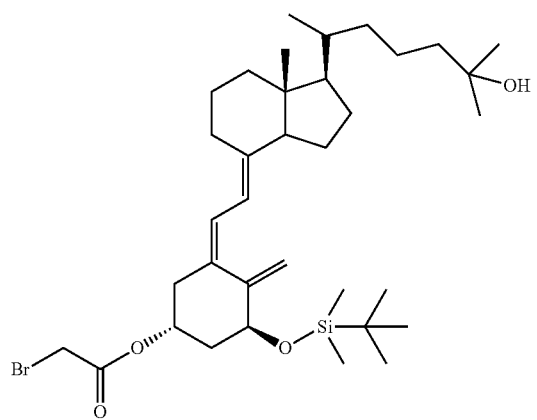

Calcidiol A-Ring Derivatives

Given that the lead compound 1 is a relatively simple derivative of calcidiol, an initial fsynthetic effort has been to prepare the fluoroacetate derivative (fluoroacetoxycalcidiol) shown as a probe for NMR studies. It is anticipated that 2 will bind to the same receptor site as 1. The fluorine nuclei incorporated in this molecule can be utilized to probe the binding site.

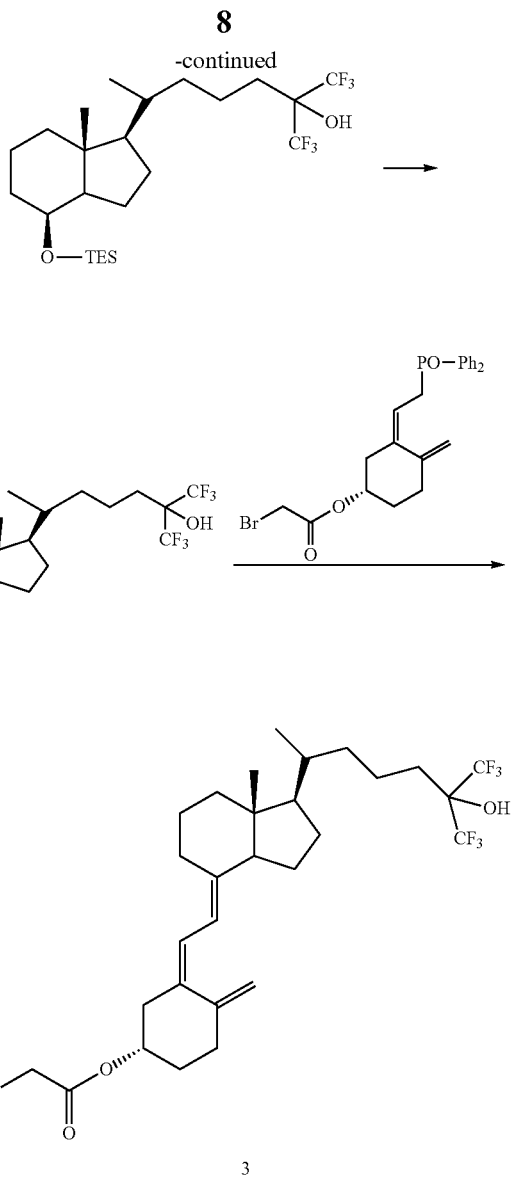

For additional NMR studies, the 25,26-hexafluororo-B3CD derivative 3 will be synthesized. A brief outline of the synthesis of compound 3 is given below following established synthetic procedures.

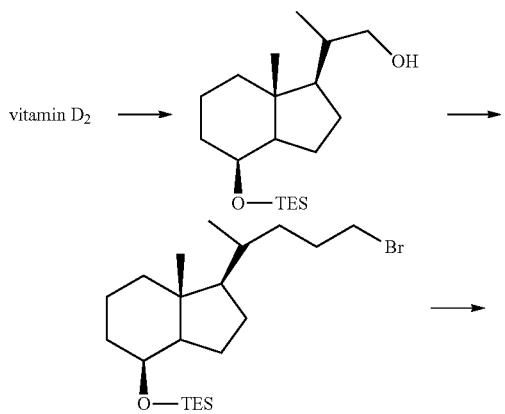

Based upon the premise that the pharmacophore in compound 1 (B3CD) is the electrophilic bromoacetate functionality, the series of A ring esterified analogs of compound 1 derivatized at the 3-hydroxy position as shown will be prepared for further evaluation in the cytotoxicity screens. The basic A ring synthon for these derivatives has been previously reported. These derivatives are proposed as first generation targets for synthesis because they incorporate readily available electrophiles at C-3. This initial list represents approximately 50-60 new A ring derivatives proposed for preparation in the first round.

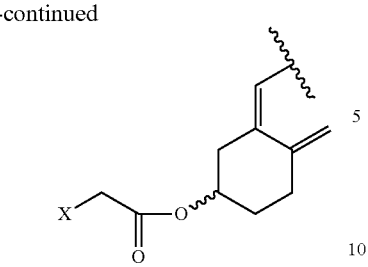
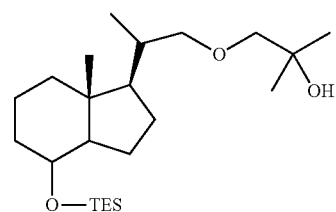

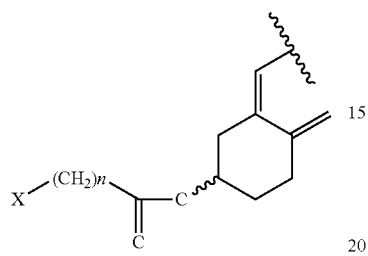
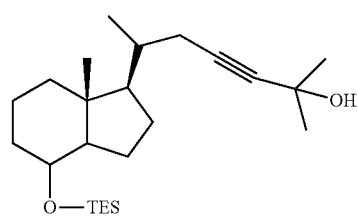

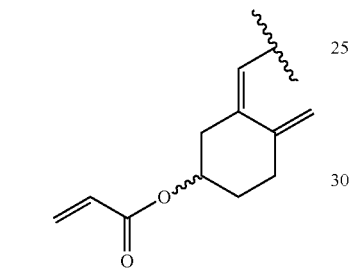
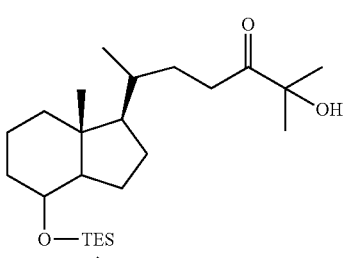

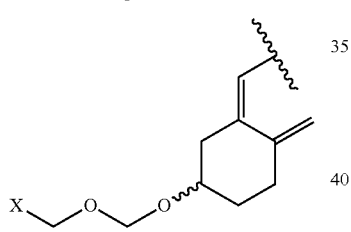
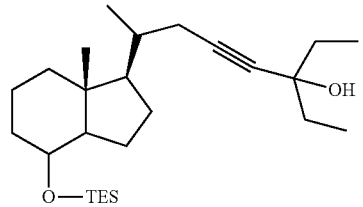

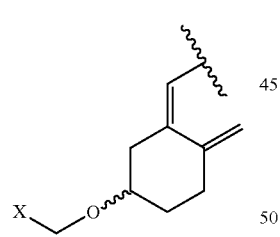
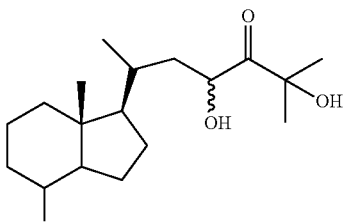

X=F, Cl, Br, I, N₃, N₂, NH₂, CN, S—CH₃

The A ring derivatives shown will be combined with a number of C-D ring synthons modified in either the side chain or are 16,17-ene analogs as shown below. Previous experience in the total synthesis of calcitriol (1,25-dihydroxy vitamin $D_3$) metabolites for the synthesis of the CD ring substructures will be employed. These initial screening set of C-D ring analogs are selected by evaluation of the numerous derivatives of calcitriol derivatives that have been reported in the literature to date. It is noteworthy that of all the compounds reported in the literature to date, there are no simple derivatives with electrophilic substitutents appended to the 3-hydroxy group as proposed.

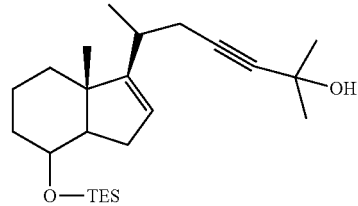

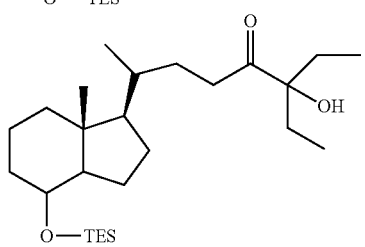

-continued

Hence, the final combination of the synthons depicted will produce a relatively small library of nearly 400-500 new compounds for screening. Although this represents a substantial effort to prepare a sample each of this many compounds individually, to date there is no rational combinatorial synthetic approach to this problem. New routes to developing a library of molecules that include three or more sites of diversity that will be more amenable to the combinatorial library synthesis will be addressed. Having developed such routes, the methodology for the preparation of a larger library of potential lead compounds will be employed.

Fluoro-derivatives of these compounds for use in NMR structural studies will also be prepared.

Larger scale synthesis of compounds identified in the initial screens that are identified as having enhanced in vitro cytotoxicity based upon the initial assays will also be developed. This larger scale synthesis will focus on providing compounds with the appropriate pharmacological profile for development as therapeutic agents for the treatment of prostate and/or ovarian cancers. It is anticipated that these synthetic efforts will require the synthesis of perhaps 10-15 compounds throughout the duration of this project on a scale of several hundred milligrams. In the ideal situation at least five compounds will be identified for promotion to animal studies. The compounds may be produced on a gram scale for such studies.

Accordingly, the invention calcidiol derivatives, and pharmaceutical compositions comprising same, having formula I:

wherein:
  $A_1$ is single or double bond;
  $A_2$ is a single, double or triple bond;
  $X_1$ and $X_2$ are each independently $H_2$ or $CH_2$, provided $X_1$ and $X_2$ are not both $=CH_2$;
    and $X_1$ can be substituted with $CH_2OR_{11}$
    wherein $R_{11}$ is C(O)alkyl, C(O)aryl, or C(O)aralkyl;
  $R_1$ is H, OH, or $OSi(R_{10})_3$;
    Wherein $R_{10}$ is alkyl, aryl, alkenyl, or aralkyl;
  $R_2$ is $O(CH_2)_nR_{12}$;
    Wherein $R_{12}$ is halogen, haloalkyl, amino, alkyl amino, thiol, alkyl thio,
    hydroxyl, alkoxy, or alkenyl;
    n is an integer from 1-6;
    and any of the $CH_2$ groups may be replaced by CO;
  $R_3$ and $R_4$ independently H, $C_1$-$C_4$ alkyl, hydroxyalkyl, or haloalkyl, or $R_3$ and $R_4$ taken
    together with $C_{20}$ form $C_3$-$C_6$ cycloalkyl;
  $R_5$ is H, $C_1$-$C_4$ alkyl, hydroxyalkyl, haloalkyl, or carbonyl;
  $R_6$ and $R_7$ are each independently alkyl or haloalkyl;
  $R_8$ is H or biotin;
  $R_9$ is H, hydroxyl, or halogen;
stereoisomers, enantiomers prodrugs thereof; and pharmaceutically acceptable esters, salts, solvates, and clathrates thereof.

In certain embodiments, the invention provides calcidiol derivatives having formula II:

wherein X is F, Cl, Br, I, $N_3$, $N_2$, $NH_2$, CN, S—$CH_3$, or —N=C=S;
R is or a pharmaceutically acceptable salt, solvate, clathrate, stereoisomer, enantiomer or prodrug thereof.

Table I is a list of illustrative compounds of the invention.

TABLE I

Bromoacetoxycalcidiol
(B3CD)
Bromo-acetic acid 3-{2-[1-
(5-hydroxy-1,5-dimethyl-
hexyl)-7a-methyl-octahydro-
inden-4-ylidene]-ethylidene}-
4-methylene-cyclohexyl ester

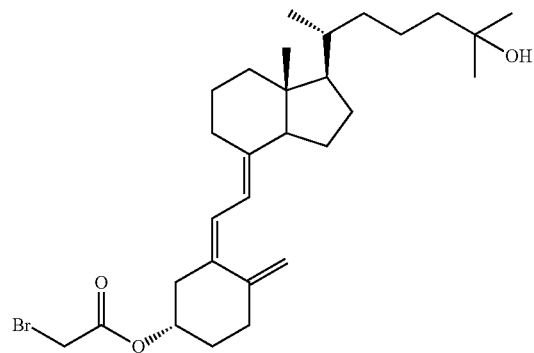 [SMILES: C=C1CC[C@H](OC(=O)CBr)C/C1=C/C=C1\CCC[C@@]2(C)C1CC[C@@H]2[C@H](C)CCCC(C)(C)O]

25-Biotin-
Bromoacetoxycalcidiol

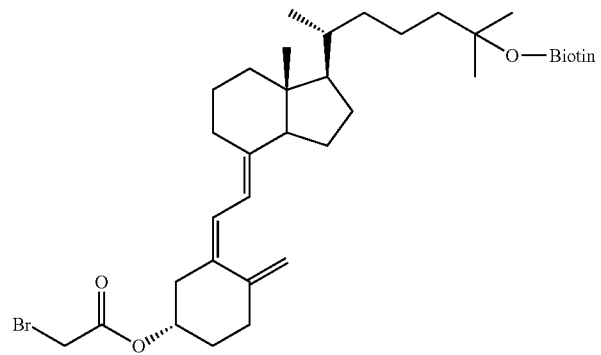

6-(2,4-Dinitro-phenylamino)-
hexanoic acid 2-(4-(2-bromo-
acetoxy)-2-{2-[1-(5-hydroxy-
1,5-
dimethyl-hexyl)-7a-methyl-
octahydro-inden-4-ylidene]-
ethylidene}-
cyclohexylidene)-ethyl ester

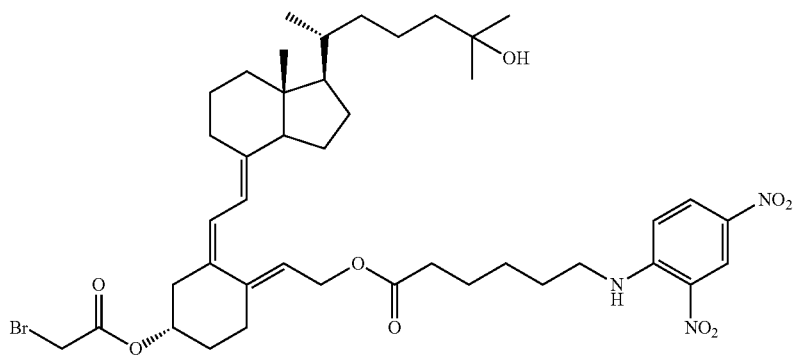 [SMILES: C[C@H](CCCC(C)(C)O)[C@H]1CCC2/C(=C/C=C3/C[C@@H](OC(=O)CBr)CC/C3=C\COC(=O)CCCCCNc3ccc([N+](=O)[O-])cc3[N+](=O)[O-])CCC[C@@]21C]

Bromo-acetic acid 3-
hydroxy-5-{2-[1-(5-hydroxy-
1,5-dimethyl-hexyl)-7a-
methyl-octahydro-inden-4-
ylide ne]-ethylidene}-4-
methylene-cyclohexyl ester

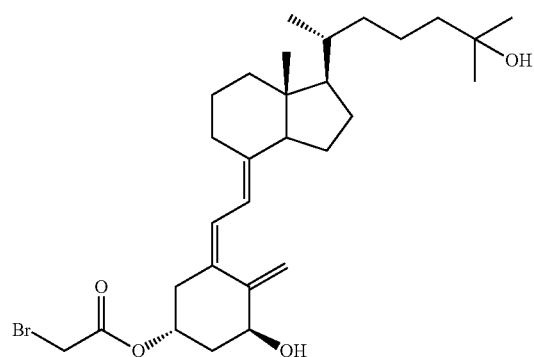 [SMILES: C=C1/C(=C\C=C2/CCC[C@@]3(C)C2CC[C@@H]3[C@H](C)CCCC(C)(C)O)C[C@@H](OC(=O)CBr)C[C@@H]1O]

TABLE I-continued

| | |
|---|---|
| Bromo-acetic acid 3-(tert-butyl-dimethyl-silanyloxy)-5-{2-[1-(5-hydroxy-1,5-dimethyl-hexyl)-7a-methyl-octahydro-inden-4-ylidene]-ethylidene}-4-methylene-cyclohexyl ester | 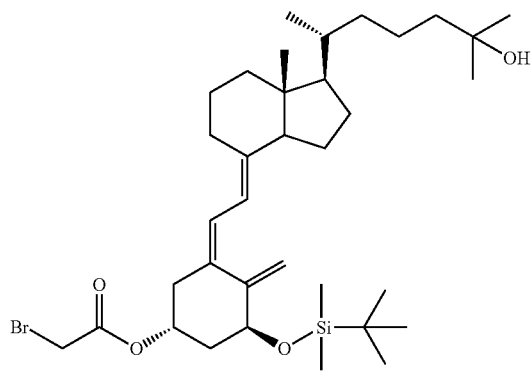 [SMILES: C=C1/C(=C\C=C2/CCC[C@@]3(C)C2CC[C@@H]3[C@H](C)CCCC(C)(C)O)C[C@@H](OC(=O)CBr)C[C@@H]1O[Si](C)(C)C(C)(C)C] |
| Trifluoro-acetic acid 3-{2-[1-(5-hydroxy-1,5-dimethyl-hexyl)-7a-methyl-octahydro-inden-4-ylidene]-ethylidene}-4-methylene-cyclohexyl ester | 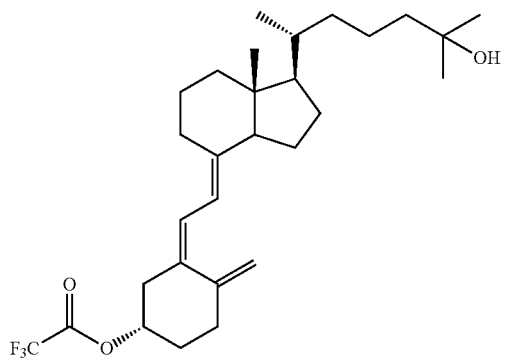 [SMILES: C=C1CC[C@H](OC(=O)C(F)(F)F)C/C1=C/C=C1\CCC[C@@]2(C)C1CC[C@@H]2[C@H](C)CCCC(C)(C)O] |
| 4-Bromo-butyric acid 3-{2-[1-(5-hydroxy-1,5-dimethyl-hexyl)-7a-methyl-octahydro-inden-4-ylidene]-ethylidene}-4-methylene-cyclohexyl ester | 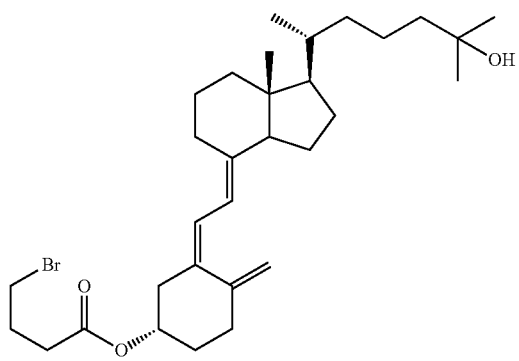 [SMILES: C=C1CC[C@H](OC(=O)CCCBr)C/C1=C/C=C1\CCC[C@@]2(C)C1CC[C@@H]2[C@H](C)CCCC(C)(C)O] |
| 4-Cyano-butyric acid 3-{2-[1-(5-hydroxy-1,5-dimethyl-hexyl)-7a-methyl-octahydro-inden-4-ylidene]-ethylidene}-4-methylene-cyclohexyl ester | 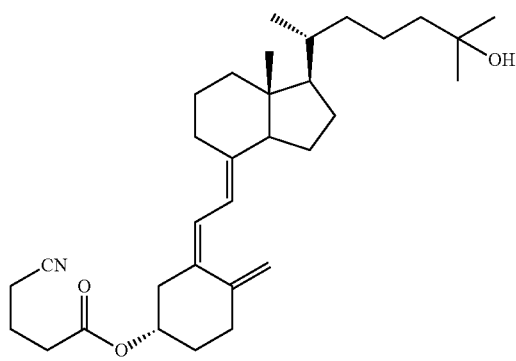 [SMILES: C=C1CC[C@H](OC(=O)CCCC#N)C/C1=C/C=C1\CCC[C@@]2(C)C1CC[C@@H]2[C@H](C)CCCC(C)(C)O] |

TABLE I-continued

| | |
|---|---|
| Acrylic acid 3-{2-[1-(5-hydroxy-1,5-dimethyl-hexyl)-7a-methyl-octahydro-inden-4-ylidene]-ethylidene}-4-methylene-cyclohexyl ester | 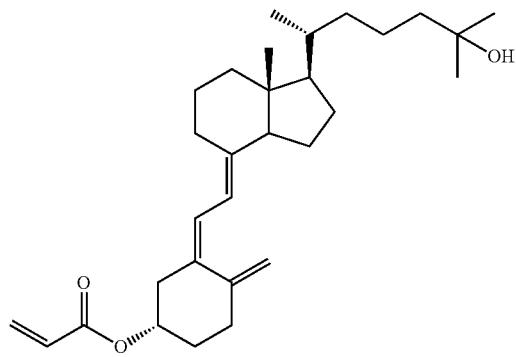 [SMILES: C=CC(=O)O[C@H]1CCC(=C)/C(=C\C=C2/CCC[C@@]3(C)C2CC[C@@H]3[C@H](C)CCCC(C)(C)O)C1] |
| 6-{4-[2-(5-Bromomethoxymethoxy-2-methylene-cyclohexylidene)-ethylidene]-7a-methyl-octahydro-inden-1-yl}-2-methyl-heptan-2-ol | 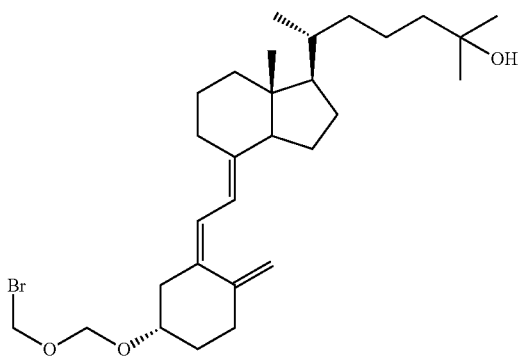 |
| 6-{4-[2-(5-Aminomethoxymethoxy-2-methylene-cyclohexylidene)-ethylidene]-7a-methyl-octahydro-inden-1-yl}-2-methyl-heptan-2-ol | 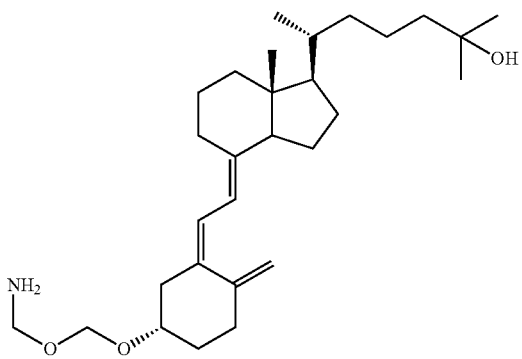 [SMILES: C=C1CC[C@H](OCOCN)C/C1=C/C=C1\CCC[C@@]2(C)C1CC[C@@H]2[C@H](C)CCCC(C)(C)O] |
| 6-{4-[2-(5-Bromomethoxy-2-methylene-cyclohexylidene)-ethylidene]-7a-methyl-octahydro-inden-1-yl}-2-methyl-heptan-2-ol | 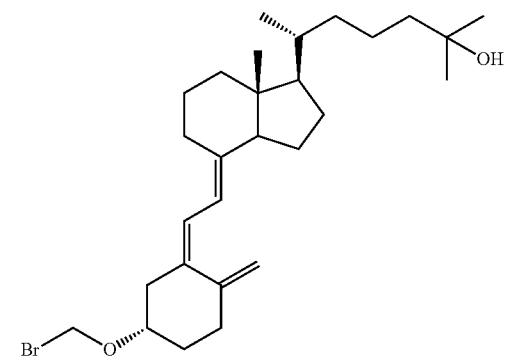 [SMILES: C=C1CC[C@H](OCBr)C/C1=C/C=C1\CCC[C@@]2(C)C1CC[C@@H]2[C@H](C)CCCC(C)(C)O] |

TABLE I-continued

2-Methyl-6-{7a-methyl-4-[2-(2-methylene-5-ethylsulfanylmethoxy-cyclohexylidene)-ethylidene]-octahydro-inden-1-yl}-heptan-2-ol

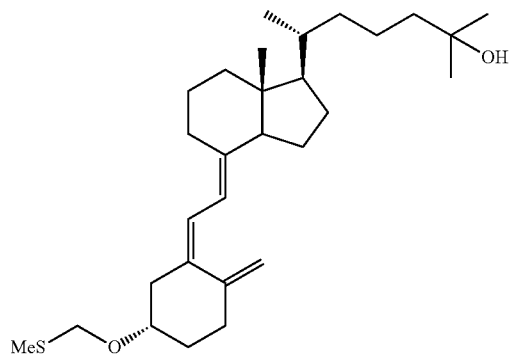 [SMILES: C=C1CC[C@H](OCSC)C/C1=C/C=C1\CCC[C@@]2(C)C1CC[C@@H]2[C@H](C)CCCC(C)(C)O]

Bromo-acetic acid 3-(2-{1-[2-(2-hydroxy-2-methyl-propoxy)-1-methyl-ethyl]-7a-methyl-octahydro-inden-4-ylidene}-ethylidene)-4-methylene-cyclohexyl ester

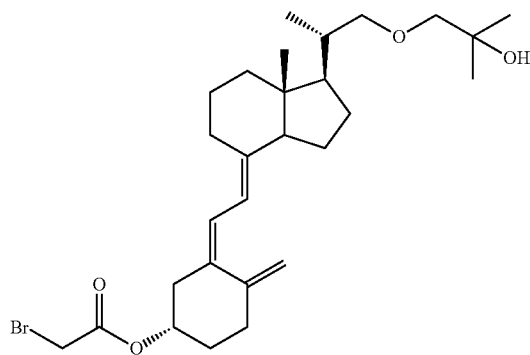 [SMILES: C=C1CC[C@H](OC(=O)CBr)C/C1=C/C=C1\CCC[C@@]2(C)C1CC[C@@H]2[C@H](C)COCC(C)(C)O]

Bromo-acetic acid 3-{2-[1-(5-hydroxy-1,5-dimethyl-hex-3-ynyl)-7a-methyl-octahydro-inden-4-ylidene]-ethylidene}-4-methylene-cyclohexyl ester

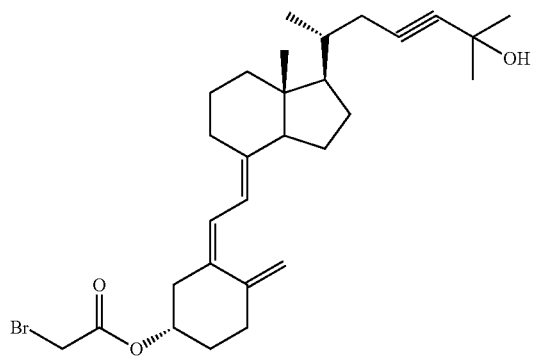 [SMILES: C=C1CC[C@H](OC(=O)CBr)C/C1=C/C=C1\CCC[C@@]2(C)C1CC[C@@H]2[C@H](C)CC#CC(C)(C)O]

Bromo-acetic acid 3-{2-[1-(5-hydroxy-1,5-dimethyl-4-oxo-hexyl)-7a-methyl-octahydro-inden-4-ylidene]-ethylidene}-4-methylene-cyclohexyl ester

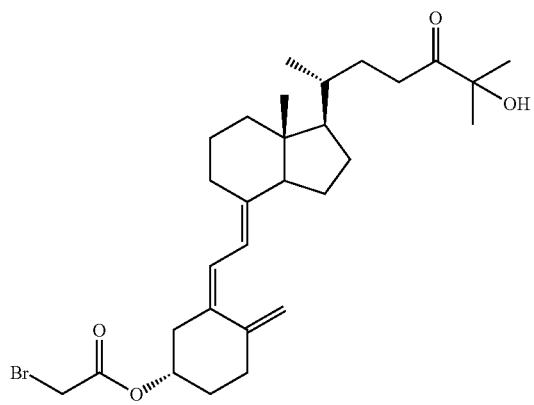 [SMILES: C=C1CC[C@H](OC(=O)CBr)C/C1=C/C=C1\CCC[C@@]2(C)C1CC[C@@H]2[C@H](C)CCC(=O)C(C)(C)O]

TABLE I-continued

Bromo-acetic acid 3-{2-[1-(5-ethyl-5-hydroxy-1-methyl-hept-3-ynyl)-7a-methyl-octahydro-inden-4-ylidene]-ethylidene}-4-methylene-cyclohexyl ester

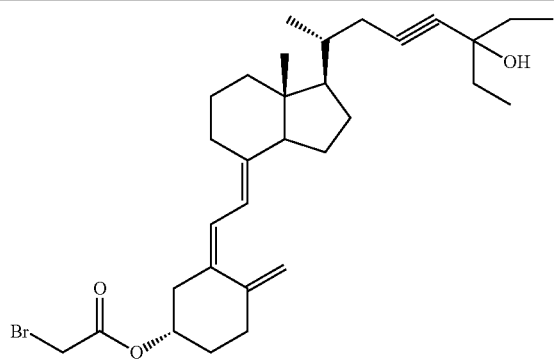 [SMILES: C=C1CC[C@H](OC(=O)CBr)C/C1=C/C=C1\CCC[C@@]2(C)C1CC[C@@H]2[C@H](C)CC#CC(O)(CC)CC]

Bromo-acetic acid 3-{2-[1-(3,5-dihydroxy-1,5-dimethyl-4-oxo-hexyl)-7a-methyl-octahydro-inden-4-ylidene]-ethylidene}-4-methylene-cyclohexyl ester

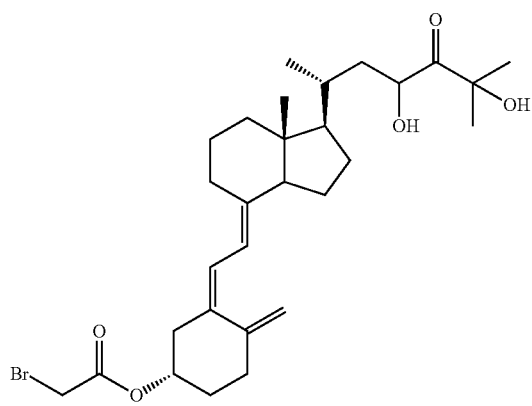 [SMILES: C=C1CC[C@H](OC(=O)CBr)C/C1=C/C=C1\CCC[C@@]2(C)C1CC[C@@H]2[C@H](C)CC(O)C(=O)C(C)(C)O]

Bromo-acetic acid 3-{2-[1-(5-hydroxy-1,5-dimethyl-hex-3-ynyl)-7a-methyl-3,3a,5,6,7,7a-hexahydro-inden-4-ylidene]-ethylidene}-4-methylene-cyclohexyl ester

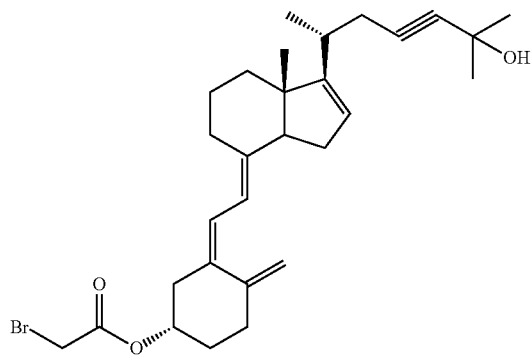

Bromo-acetic acid 3-{2-[1-(5-ethyl-5-hydroxy-1-methyl-4-oxo-heptyl)-7a-methyl-octahydro-inden-4-ylidene]-ethylidene}-4-methylene-cyclohexyl ester

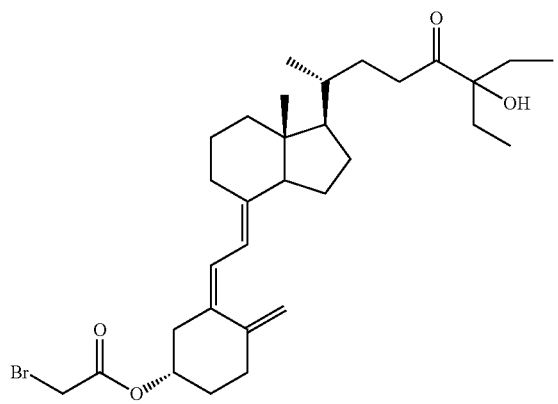 [SMILES: C=C1CC[C@H](OC(=O)CBr)C/C1=C/C=C1\CCC[C@@]2(C)C1CC[C@@H]2[C@H](C)CCC(=O)C(O)(CC)CC]

TABLE I-continued

Bromo-acetic acid 3-(2-{1-[1-(4-hydroxy-4-methyl-3-oxo-pentyl)-cyclopropyl]-7a-methyl-octahydro-inden-4-ylidene}-ethylidene)-4-methylene-cyclohexyl ester

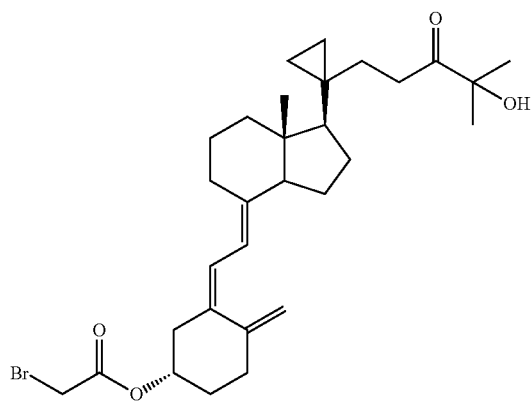 [SMILES: C=C1CC[C@H](OC(=O)CBr)C/C1=C/C=C1\CCC[C@@]2(C)C1CC[C@@H]2C1(CCC(=O)C(C)(C)O)CC1]

Bromo-acetic acid 4-methylene 3-{2-[7a-methyl-1-(6,6,6-trifluoro-5-hydroxy-1-methyl-5-trifluoromethyl-hexyl)-octahydro-inden-4-ylidene]-ethylidene}-cyclohexyl ester

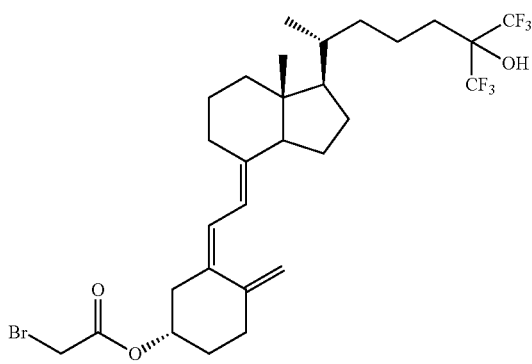 [SMILES: C=C1CC[C@H](OC(=O)CBr)C/C1=C/C=C1\CCC[C@@]2(C)C1CC[C@@H]2[C@H](C)CCCC(O)(C(F)(F)F)C(F)(F)F]

3-(4-{2-[5-(2-Bromo-acetoxy)-2-methylene-cyclohexylidene]-ethylidene}-7a-methyl-octahydro-inden-1-yl)-butyric acid

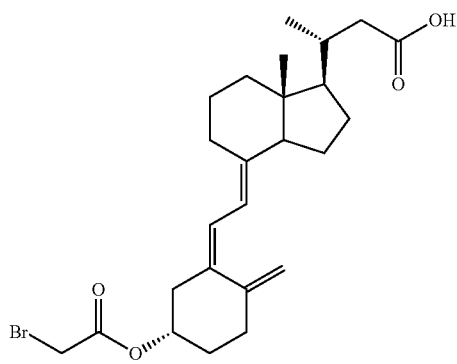 [SMILES: C=C1CC[C@H](OC(=O)CBr)C/C1=C/C=C1\CCC[C@@]2(C)C1CC[C@@H]2[C@H](C)CC(=O)O]

In one embodiment, a calcidiol derivative in accordance with the invention is is bromoacetoxycalcidiol (abbreviated "B3CD"). This compound is also know as bromoacetic acid 3-{2-[1-(5-hydroxy-1,5-dimethyl-hexyl)-7a-methyl-octahydro-inden-4-ylidene]-ethylidene}-4-methylene-cyclohexyl ester, the structure of which is as follows:

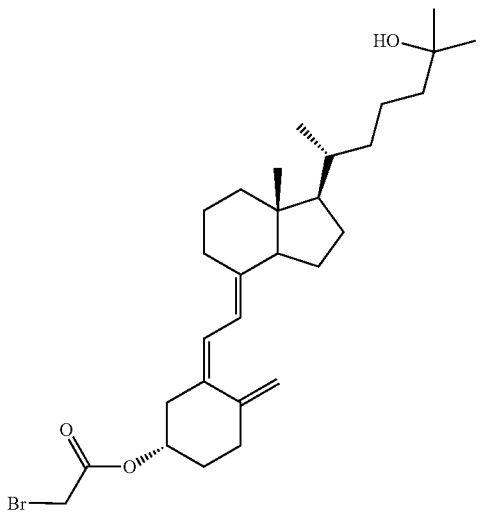 [SMILES: C=C1CC[C@H](OC(=O)CBr)C/C1=C/C=C1\CCC[C@@]2(C)C1CC[C@@H]2[C@H](C)CCCC(C)(C)O]

A pharmaceutically acceptable salt, solvate, clathrate, stereoisomer, enantiomer, or prodrug of this compound is also provided.

The terms "analog" and "derivative" are used interchangeably. As used herein a "calcidiol analog" or a "calcidiol derivative" refers to a compound which retains chemical structures of calcidiol necessary for the desired functional activity of calcidiol derivatives (e.g., the A and C-D ring structures), yet which also contains certain chemical structures which differ from that of calcidiol (e.g., modifications in the side chain and at carbon 3 of the A ring).

The term "alkyl" refers to the radical of saturated aliphatic groups, including straight-chain alkyl groups, and branched-chain alkyl groups. The term alkyl further includes alkyl groups, which can further include oxygen, nitrogen, sulfur or phosphorous atoms replacing one or more carbons of the hydrocarbon backbone, e.g., oxygen, nitrogen, sulfur or phosphorous atoms. In preferred embodiments, a straight chain or branched chain alkyl has 30 or fewer carbon atoms in its backbone (e.g., $C_1$-$C_{30}$ for straight chain, $C_3$-$C_{30}$ for branched chain), preferably 26 or fewer, and more preferably 20 or fewer, and still more preferably 4 or fewer.

Moreover, the term alkyl as used throughout the specification and claims is intended to include both "unsubstituted alkyls" and "substituted alkyls," the latter of which refers to alkyl moieties having substituents replacing a hydrogen on one or more carbons of the hydrocarbon backbone. Such substituents can include, for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. It will be understood by those skilled in the art that the moieties substituted on the hydrocarbon chain can themselves be substituted, if appropriate.

The term "alkyl" also includes unsaturated aliphatic groups analogous in length and possible substitution to the alkyls described above, but that contain at least one double or triple bond respectively. An "alkylaryl" moiety is an alkyl substituted with an aryl (e.g., phenylmethyl(benzyl)).

The terms "alkoxy," "aminoalkyl" and "thioalkoxy" refer to alkyl groups, as described above, which further include oxygen, nitrogen or sulfur atoms replacing one or more carbons of the hydrocarbon backbone, e.g., oxygen, nitrogen or sulfur atoms.

The terms "alkenyl" and "alkynyl" refer to unsaturated aliphatic groups analogous in length and possible substitution to the alkyls described above, but that contain at least one double or triple bond, respectively. For example, the invention contemplates cyano and propargyl groups.

The term "aralkyl" means an aryl group that is attached to another group by a ($C_1$-$C_6$)alkylene group. Aralkyl groups may be optionally substituted, either on the aryl portion of the aralkyl group or on the alkylene portion of the aralkyl group, with one or more substituents.

The term "aryl" as used herein, refers to the radical of aryl groups, including 5- and 6-membered single-ring aromatic groups that may include from zero to four heteroatoms (heteroaryl), for example, benzene, pyrrole, furan, thiophene, imidazole, benzoxazole, benzothiazole, triazole, tetrazole, pyrazole, pyridine, pyrazine, pyridazine and pyrimidine, and the like. Aryl groups also include polycyclic fused aromatic groups such as naphthyl, quinolyl, indolyl, and the like.

Those aryl groups having heteroatoms in the ring structure may also be referred to as "heteroaryls" or "heteroaromatics." The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "cyclyl" refers to a hydrocarbon 3-8 membered monocyclic or 7-14 membered bicyclic ring system having at least one non-aromatic ring, wherein the non-aromatic ring has some degree of unsaturation. Cyclyl groups may be optionally substituted with one or more substituents. In one embodiment, 0, 1, 2, 3, or 4 atoms of each ring of a cyclyl group may be substituted by a substituent. The term "cycloalkyl" refers to a hydrocarbon 3-8 membered monocyclic or 7-14 membered bicyclic ring system having at least one saturated ring. Cycloalkyl groups may be optionally substituted with one or more substituents. In one embodiment, 0, 1, 2, 3, or 4 atoms of each ring of a cycloalkyl group may be substituted by a substituent. Cycloalkyls can be further substituted, e.g., with the substituents described above. Preferred cyclyls and cycloalkyls have from 3-10 carbon atoms in their ring structure, and more preferably have 3, 4, 5, 6 or 7 carbons in the ring structure. Those cyclic groups having heteroatoms in the ring structure may also be referred to as "heterocyclyl,"

"heterocycloalkyl" or "heteroaralkyl." The aromatic ring can be substituted at one or more ring positions with such substituents as described above.

The terms "cyclyl" or "cycloalkyl" refer to the radical of two or more cyclic rings (e.g., cycloalkyls, cycloalkenyls, cycloalkynyls, aryls, heteroaryls, and/or heterocyclyls). In some cases, two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, alkyl, alkylaryl, or an aromatic or heteroaromatic moiety.

The term "haloalkyl" is intended to include alkyl groups as defined above that are mono-, di- or polysubstituted by halogen, e.g., fluoromethyl and trifluoromethyl.

The term "halogen" designates —F, —Cl, —Br or —I.

The term "hydroxyl" means —OH.

The term "heteroatom" as used herein means an atom of any element other than carbon or hydrogen. Preferred heteroatoms are nitrogen, oxygen, sulfur and phosphorus.

The term "mercapto" refers to a —SH group.

The term "sulfhydryl" or "thiol" means —SH.

The compounds of the invention encompass various isomeric forms. Such isomers include, e.g., stereoisomers, e.g., chiral compounds, e.g., diastereomers and enantiomers.

The term "chiral" refers to molecules which have the property of non-superimposability of the mirror image partner, while the term "achiral" refers to molecules which are superimposable on their mirror image partner.

The term "diastereomers" refers to stereoisomers with two or more centers of dissymmetry and whose molecules are not mirror images of one another.

The term "enantiomers" refers to two stereoisomers of a compound which are non-superimposable mirror images of one another. An equimolar mixture of two enantiomers is called a "racemic mixture" or a "racemate."

The term "isomers" or "stereoisomers" refers to compounds which have identical chemical constitution, but differ with regard to the arrangement of the atoms or groups in space.

Furthermore the indication of configuration across a carbon-carbon double bond can be "Z" referring to what is often referred to as a "cis" (same side) conformation whereas "E" refers to what is often referred to as a "trans" (opposite side) conformation. Regardless, both configurations, cis/trans and/or Z/E are contemplated for the compounds for use in the present invention.

With respect to the nomenclature of a chiral center, the terms "d" and "l" configuration are as defined by the IUPAC Recommendations. As to the use of the terms, diastereomer, racemate, epimer and enantiomer, these will be used in their normal context to describe the stereochemistry of preparations.

Natural amino acids represented by the compounds utilized in the present invention are in the "l" configuration, unless otherwise designated. Unnatural or synthetic amino acids represented by the compounds utilized in the present invention are in the "d" configuration, unless otherwise designated.

Another aspect is a radiolabeled compound of any of the formulae delineated herein. Such compounds have one or more radioactive atoms (e.g., $^3$H, $^2$H, $^{14}$C, $^{13}$C, $^{35}$S, $^{32}$P, $^{125}$I, $^{131}$I) introduced into the compound. Such compounds are useful for drug metabolism studies and diagnostics, as well as therapeutic applications.

The term "obtaining" as used in obtaining the calcidiol derivative or obtaining bromoacetoxycalcidiol as used herein is intended to include purchasing, synthesizing or otherwise acquiring the calcidiol derivative or obtaining the bromoacetoxycalcidiol.

The term "prodrug" includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionoic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Preferred prodrug moieties are propionoic acid esters and acyl esters. Prodrugs which are converted to active forms through other mechanisms in vivo are also included.

Lane 1 is DNA size standard; lane 2 is SK-N-SH control; lane 3 is SH-SY5Y control; lane 4 is SK-N-SH+B3CD; lane 5 is SH-SY5Y+B3CD.

Figures 8, 9:
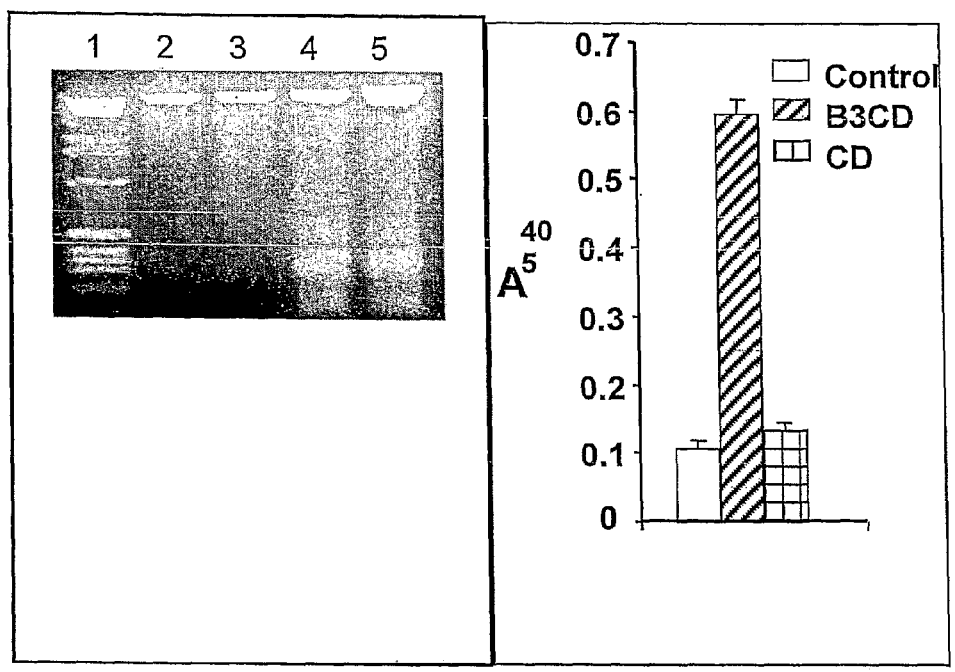
FIG. 8. B3CD is a potent inducer of apoptosis in NB cells.

FIG. 9. Activation of caspase-3 in SK-N-SH cells.

FIG. 10A. Caspase-3 immunoblot.

FIG. 10B. Caspase-9 immunoblot.

FIG. 10C. Cyt-C immunoblot of cytosol of NB cells: A and D-SMS-KCNR; B and E-5H-SY5Y and C and F-IMR-32.

FIG. 10D. Caspase-8 immunoblot.

FIG. 11. Caspase-9 inhibitor, Z-LEDH-FMK inhibits B3CD induced apoptosis.

Figures 12A, 12B:
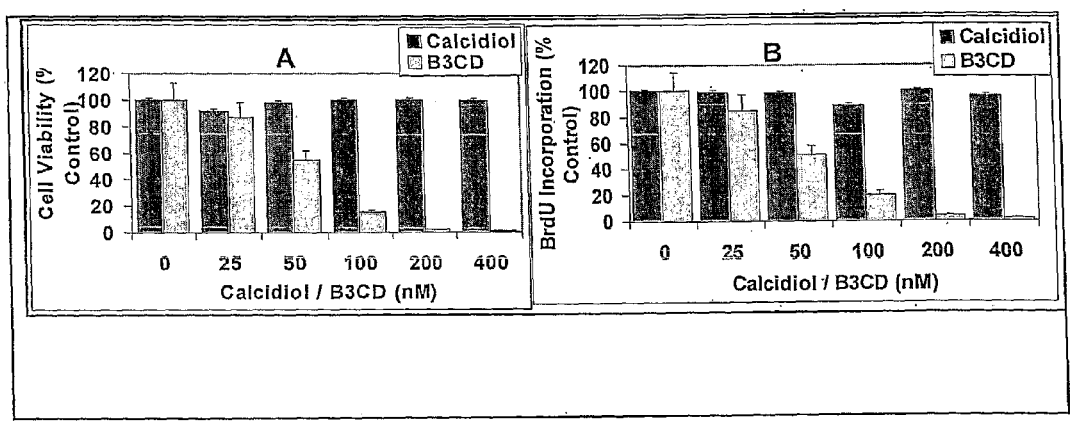

FIG. 12A. B3CD inhibits proliferation of EC; cell viability assay

FIG. 12B. BrdU incorporation assay.

Figure 13:
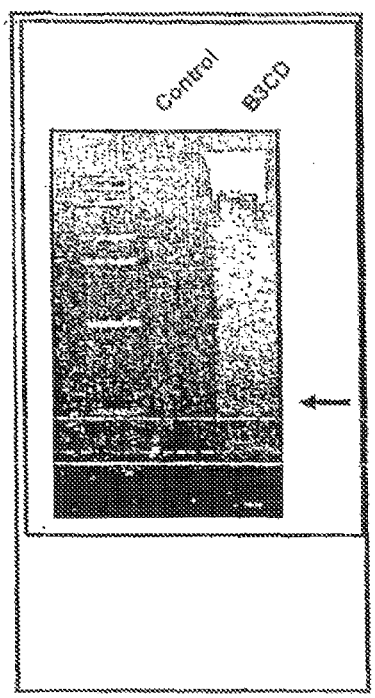

FIG. 13. DNA fragmentation analysis of B3CD treated EC.

Figure 14:
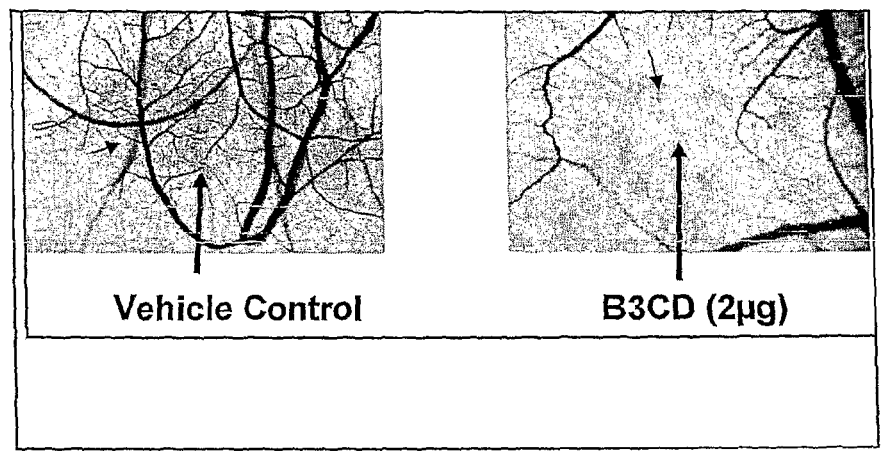

FIG. 14. B3CD inhibits angiogenesis.

FIG. 15A. Toxicity studies of B3CD in mice showing effect on body weight.

FIG. 15B. Toxicity studies of B3CD in mice showing effect on serum calcium.

DETAILED DESCRIPTION OF THE INVENTION

Neuroblastoma (NB) is predominantly a tumor of early childhood. It is the most common extracranial solid tumor, with two thirds of the cases presenting in children younger than 5 years of age. There are approximately 500-1000 new cases of NB in the U.S. each year (Weinstein J L, Katzenstein H M, Cohn S L. Advances in the diagnosis and treatment of neuroblastoma. *Oncologist.* 2003; 8:278-292). NB accounts for 7-10% of all childhood cancers, and it is the most common cancer diagnosed during infancy. The hallmark of neuroblastoma is clinical heterogeneity: Some tumors regress spontaneously, whereas others differentiate into benign ganglion-euromas. Unfortunately, the majority of patients over 1 year of age develop locally aggressive and/or metastatic fatal disease.

As classified by International Neuroblastoma Staging System (INSS) there are six stages of neuroblastoma; Stage 1 (localized resectable), Stage 2a and 2b (localized unresectable or ipsilateral lymph node involvement), Stage 3 (regional, unresectable and crossing the midline), Stage 4 (disseminated) and Stage 4S (localized with limited spread; less than one year of age) referred to as "special" NB. Presenting signs and symptoms of children with NB reflect both the location of the primary tumor and the extent of disease. Patients with localized disease are often asymptomatic, while children with metastatic disease typically appear ill at presentation with systemic symptoms, including fever and bone pain. About 40% of children with NB respond to radiation and single agent chemotherapy. These patients are considered the 'low-risk' group characterized by lack of N-myc amplification. Patients with metastatic NB are considered the 'high-risk' group. Their tumors generally demonstrate amplification of the N-myc proto-oncogene, contain poorly differentiated cells, and respond poorly to conventional chemo- and radiotherapies (Maris J M, Matthay K K. (1999) Molecular biology of neuroblastoma. *J Clin Oncol.* 17:2264-2279). Very occasionally NB tumors undergo spontaneous regression or differentiate into benign ganglioneuromas. At the time of diagnosis, approximately 50% of infants and 70% of older NB patients have disseminated disease spread beyond the primary site to lymph nodes, bone marrow, and liver.

Treatment methods currently available are used either singly or in combination depending on the location, biological characteristics of the cancer cells, stage and risk group to which the patient belongs to (low, intermediate and high risk). These include surgery, radiation therapy, chemotherapy and bone marrow or stem cell transplantation. Low-risk NB patients require minimal therapy; excellent outcome is also seen in patients with stages 2A and 2B disease. Intermediate-risk patients with favorable biology tumors are treated with a short course of chemotherapy (four cycles), while intermediate-risk patients with unfavorable biology receive a longer course of chemotherapy (eight cycles).

However, these procedures do not produce desired satisfactory results. Hence, developing new therapeutic modalities is vital in order to improve the outcome for patients with NB. New lines of treatment procedures are being developed. They include use cytotoxic agents (topotecan, a topoisomerase I inhibitor, cisplatin, doxorubicin, and cyclophosphamides, either alone or in combination) retinoids (13-cis-RA, all-trans-RA and fenretinide), immunotherapy (anti-GD2 antibodies), cytokines (GM-CSF and IL2) radioiodinated meta-iodobenzylguanidine (to target delivery of radiotherapy). Unfortunately, survival for high-risk children has improved only modestly during the past 20 years. This improvement is thought to be due to intensification of induction chemotherapy, megatherapy consolidation, and improved supportive care. Despite intensive multimodality treatment, more than 50% of children with high-risk disease will relapse due to drug-resistant residual disease. Eradication of refractory microscopic disease remains one of the most significant challenges in the treatment of high-risk NB.

Role of Angiogenesis in Neuroblastoma.

Angiogenesis, the development of new blood vessels from the existing vasculature, is an essential component of solid tumor growth and metastasis. It is well established that a proliferating tumor mass, whether the primary tumor or a small clump of cells lodged at a distant metastatic site, can only reach microscopic size before physical constraints prevent the essential supply of nutrients. Therefore, tumors establish their own vasculature in order to be able to survive and grow.

In 1994, Kleinman and colleagues showed that human neuroblastoma cells induce angiogenesis in the nude mouse during tumorigenesis (Kleinman N R, Lewandowska K, Culp L A. Tumour progression of human neuroblastoma cells tagged with a lacZ marker gene: earliest events at ectopic injection sites. *Br J Cancer.* 1994; 69:670-679). An increased expression of several angiogenic factors like VEGF, FGF, Angiopoietin, TGF-α and PDGF have been shown to be strongly correlated with advanced stage neuroblastoma. In NB, high-level expression of angiogenesis activators and high tumor vascularity has been shown to correlate with advanced-staged disease. Preclinical studies have demonstrated that antiangiogenic agents effectively inhibit NB growth in vivo. These observations suggest that angiogenesis inhibitors may be effective in the treatment of patients with highly vascular tumors such as NB. Although essential in the developing embryo, angiogenesis in the adult is limited to menstruation and wound healing. Therefore, a targeted inhibitor of angiogenesis may arrest the growth of the primary tumor, and subsequent metastases, with far less chance for resistance to develop. Drugs that target endothelial cells should be effective against a wide variety of solid tumors including neuroblastoma.

Despite progress in chemotherapy, many chemical agents become ineffective and may cause serious side effects due to toxicity of high dosages required to prevent cancer growth. The present invention identifies a class of compounds that show promise as improved therapeutics for treatment of cancers, particularly for aggressive cancers such as neuroblastomas.

An exemplary compound, a bromoacetoxy derivative of calcidiol (B3CD), is shown to be a potent antiproliferative and apoptotic agent with respect to neuroblastoma cells. BDNF mediated chemoprotection of the cells was suppressed by inhibiting TrkB signaling. Surprisingly, B3CD inhibited angiogenesis, thus suggesting it as a prime chemotherapeutic agent candidate for tumors such as neuroblastoma. Its activity against several types of cancer cells further indicated its potential utility as a general cancer chemotherapeutic.

Pharmaceutical Compositions

Pharmaceutical compositions and dosage forms of the invention comprise one or more active ingredients in relative amounts and formulated so that a given pharmaceutical composition or dosage form inhibits cancer cell proliferation. Preferred pharmaceutical compositions and dosage forms comprise a compound of formula I or a pharmaceutically acceptable prodrug, salt, solvate or clathrate thereof, optionally in combination with one or more additional active agents.

Compositions containing the chemotherapeutic agent may be administered in several ways, including orally, parenterally, intraperitoneally, intradermally or intramuscularly. Pharmaceutical forms suitable for injection include sterile aqueous solutions or dispersions for extemporaneous preparation of the solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol and liquid polyethylene glycol, and the like), suitable mixtures thereof, and vegetable oils. The proper fluidity can be maintained by the use of a coating such as lecithin, by the maintenance of the required particle size in case of a dispersion and by the use of surfactants. The prevention of the action of microorganisms can be effected by various antibacterial and antifungal agents such as parabens, chlorobutanol, phenol, sorbic acid, thimerosal and the like. In many cases, isotonic agents may be included, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Oral dosage forms are also contemplated. Pharmaceutical compositions of the invention that are suitable for oral administration can be presented as discrete dosage forms, including but not limited to, tablets (e.g. chewable tablets), caplets, capsules and liquids such as flavored syrups. Dosage forms containing predetermined amounts of active ingredients may be prepared by well known methods of pharmacy, see *Remington's Pharmaceutical Sciences* (1990) 18$^{th}$ ed., Mack Publishing Co., Easton, Pa.

Typical oral dosage forms of the invention are prepared by combining the active ingredient(s) in an admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms of the invention include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivates (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. One specific binder is a mixture of microcrystalline cellulose and sodium carboxymethyl cellulose sold as AVICEL RC-581. Suitable anhydrous or low moisture excipients or additives include AVICEL-PH-103J and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pregelatinized starch, and mixtures thereof. The binder or filler in pharmaceutical compositions of the invention is typically present in from about 50 to about 99 weight percent of the pharmaceutical composition or dosage form.

Disintegrants are used in the compositions of the invention to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms of the invention. The amount of disintegrant used varies based upon the type of formulation, and is readily discernible to those of ordinary skill in the art. Typical pharmaceutical compositions comprise from about 0.5 to about 15 weight percent of disintegrant, preferable from about 1 to about 5 weight percent of disintegrant.

Disintegrants that can be used in pharmaceutical compositions and dosage forms of the invention include, but are not limited to, agar-agar, alginic acid, calcium carbonate, microcrystalline cellulose, croscarmellose sodium, crosprovidone, polacrilin potassium, sodium starch glycolate, potato or tapioca starch, other starches, pre-gelatinized starch, other starches, clays, other algins, other cellulosses, gums, and mixtures thereof.

Lubricants that can be used in pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL 200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The pH of a pharmaceutical composition or dosage form, or of the tissue where the composition or dosage form is applied, may be adjusted to improve delivery of one or more active ingredients. Similarly, the polarity of a solvent carrier, its ionic strength, or tonicity can be adjusted to improve delivery. Compounds such as stearates can also be added to pharmaceutical compositions or dosage forms to advantageously alter the hydrophilicity or lipophilicity of one or more active ingredients to improve delivery. Stearates for example can serve as a lipid vehicle for the formulation, as an emulsifying agent or surfactant, and as a delivery-enhancing or penetration-enhancing agent. Salts, hydrates or solvates of the active ingredients can be used to further adjust the properties of the resulting compositions.

Upon formulation, solutions will be administered in a manner compatible with the dosage formulation and in such amount as is therapeutically effective. The formulations are easily administered in a variety of dosage forms preferably as injectable solutions.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous, intradermal and intraperitoneal administration. In this connection, sterile aqueous media that can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are provided as illustrations of the invention and are in no way to be considered limiting The compounds of this invention can be prepared by methods well known in the art, as well as by the synthetic routes disclosed herein.

Example 1

Analogs of B3CD

Figure 2A:
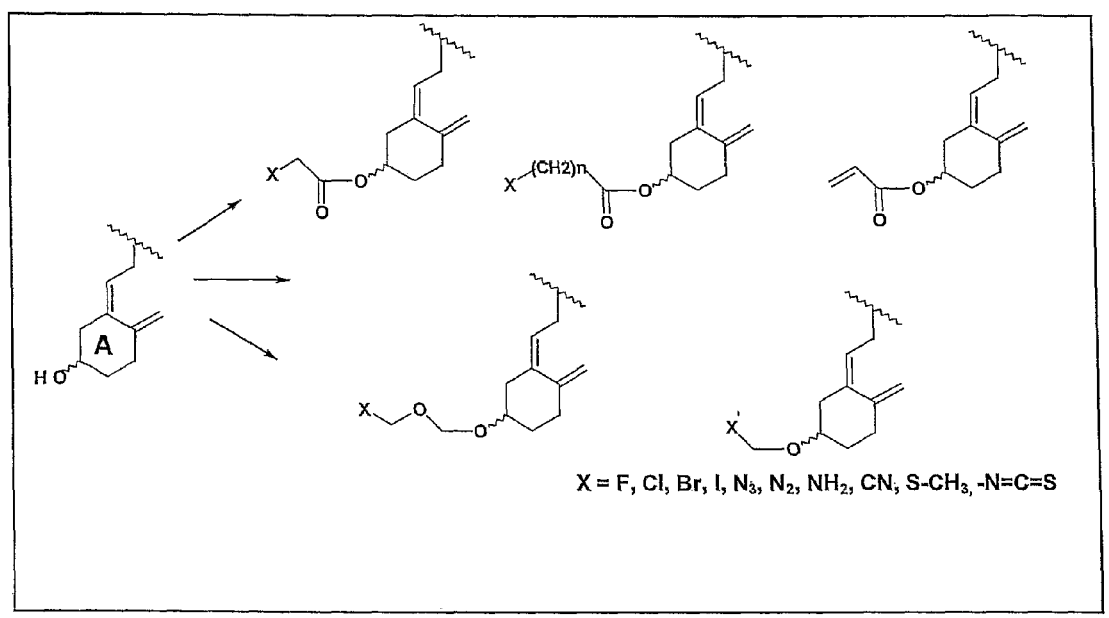
FIG. 2A. shows Chemical structure of several related calcidiol derivatives.

Derivatization of the A-ring hydroxyl group of calcidiol with bromoacetic acid imparted remarkable anticancer activity to B3CD. A library of compounds based on the B3CD scaffold will be designed and developed to improve the B3CD structure-activity profile by stepwise structural changes. A series of A-ring analogs of B3CD derivatized at the 3-OH position will be prepared (FIG. 2A). The basic A-ring synthon for these derivatives has been previously reported and readily incorporate electrophiles at C-3 position of A-ring (Frosch, J V, Lythogoe, B and Sakense, A K. Calciferal and its Derivatives. XVII. Ring A Components for synthetic work on vitamin D3 and on model compounds, *J. Chem. Soc.: Organic-BioOrganic Chem* 1974, 17:2005-2009). The important features of new derivatives will include replacement of —Br functionality with —F, —Cl, —Br, —I, —$N_3$, —$N_2$, —$NH_2$, —CN, —S—$CH_3$, and —N=C=S functionalities. The chain length between the A-ring and the functionality will be varied systematically (e.g., 2, 3, 4 . . . atoms). Importantly, the ester bond will be stabilized; more stable bonds like ether and amide bonds will be used. Traditional synthetic organic schemes and combinatorial-split and pool techniques will be used. This procedure is expected to generate 30-40 compounds initially. These compounds will be tested for anticancer activity to identify active compounds.

Figure 2B:
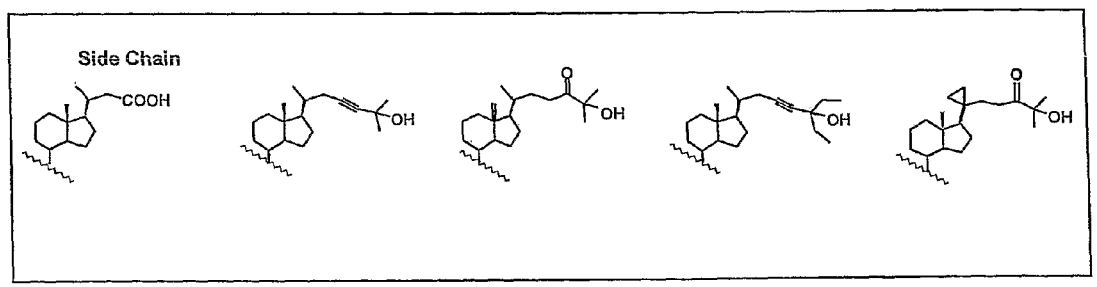
FIG. 2B. Chemical structure of side-chain modified calcidiol derivatives

To develop additional analogs, side-chain modified derivatives of the successful compounds from above will be prepared. The A ring derivatives shown in FIG. 2A can be combined with a number of side chain modified C-D ring synthons (FIG. 2B) using known synthesis techniques.

The invention also provides calcidiol derivatives that are biotinylated

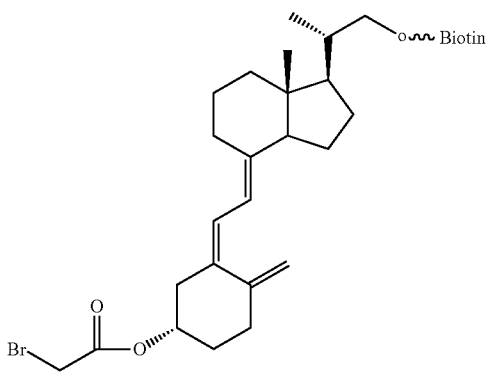

derivatives.

The purpose is to isolate and identify the target proteins and molecules that interact with B3CD in given cancer cell. A large quantity of cells will be treated with the biotinyl-derivative, the cells will be lysed, membrane, nuclear and cytosolic components will be separated and streptavidin-agarose will be used to pull down the biotinyl-derivative and any interacting protein molecule/s. The molecules will be identified by LC-MS (the regularly used procedure of MALDI-TOF)

Example 2

Anticancer Activity

A panel of cancer cells is used to evaluate the antiproliferative and cytotoxic activities of B3CD and related analogs. The cells include colon (Colo), breast (MCF-7 and MDA-MB-231), lung (A549), prostate PC3 and LNCaP), melanoma (SK-MEL-31), renal (Caki-1), ovarian (OVCAR-3), bladder (T24), pancreatic (BxPC-3), hepatocarcinoma (Hep3B), neuroblastoma (SH-SY5Y), glioblastoma (SNB-19), medulloblastoma (D283 Med), skin (LS123), squamous cell carcinoma (Scc-15), acute promyelocytic leukemia (APL), myeloblastic (HL-60) and myelomonocytic (U937).

The anticancer activity testing will be carried out by high throughput screening. The cancer cells will be cultured in 96 well plates and treated with the library. B3CD has been tested in this system and was effective at a 200 nM dose. For general screening, 2-200 nM doses will be used. Cells will be treated with the compounds for 12, 24, 48 and 72 hours. A 96 well plate format allows testing a large number of compounds simultaneously. An MTS based colorimetric method of evaluation of proliferation will be utilized, which is widely used in cancer drug discovery. The fingerprint of profiled drugs using 60 cell-line screening program by NCl using COMPARE algorithm (Paull K D, Shoemaker R H, Hodes L, Monks A, Scudiero D A, Rubinstein L, Plowman J, Boyd M R. Display and analysis of patterns of differential activity of drugs against human tumor cell lines: development of mean graph and COMPARE algorithm. *J Natl Cancer Inst* 1989; 81:1088).

B3CD, will be used as a control and its activity will be set as 100 (arbitrary units). The relative antiproliferative activities of the test compounds will be measured and expressed as percent activity of B3CD. The compounds with highest anticancer activity will be further examined. Effect on DNA synthesis (proliferation) will be determined by using BrdU incorporation assay. Apoptotic activity of the active compounds will be determined by TUNEL assays using BrdU labeling and followed by FACS. The BD BioFACS Canto instrument at Kilguss building allows a 24 well format high throughput cell sorting. Apoptotic activity of the active compounds will be expressed relative to that of B3CD. This strategy aids in identifying the most potent compounds. The successful compounds will be tested for antiangiogenic activity using CAM assay, aortic ring assay and matrigel plug assays. Similarly, the successful compounds will be tested for its general systemic toxicity.

Example 3

In Vitro Treatment of Neuroblastoma Cells

Materials and methods. Proliferation was measured by MTS and BrdU incorporation assays. Apoptosis was assessed by DNA fragmentation, Cell Death Detection ELISA and caspase-3-assays. Effect of B3CD on TrkB signaling by BDNF was assessed by Western Blot analysis of AKT and ERK phosphorylation. The effect on angiogenesis was determined by chick chorioallantoic membrane (CAM) assay and aortic ring assay.

Figure 3:
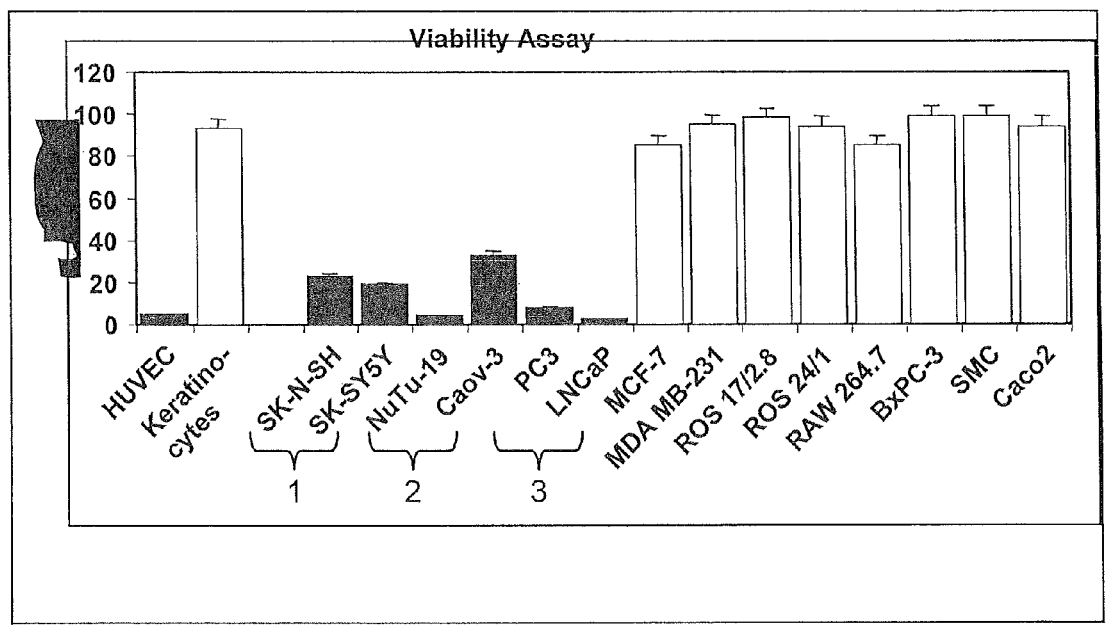
FIG. 3. B3CD selectively inhibits proliferation of endothelial cells, neuroblastic (1), ovarian (2) and prostate (3) cancer cells.
Figures 4A, 4B:
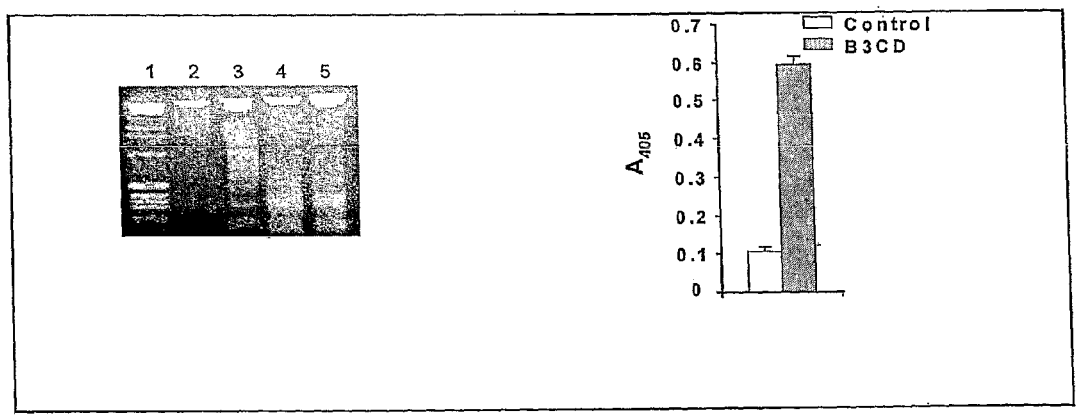
FIG. 4A. DNA fragmentation analysis of apoptosis by B3CD. 1-size standard; 2-keratinocytes; 3-neuroblastic; 4-ovarian and 5-prostate cancer cells.
FIG. 4B. Caspase-3 activation in neuroblastic cells by B3CD.

B3CD was tested on the panel of cell described above. B3CD showed potent antiproliferative and cytotoxic effects on neuroblastic, ovarian, endothelial cells and prostate cancer cells, but did not show an effect on proliferation of skin, smooth muscle, breast, pancreatic, osteosarcoma and macrophage cells (FIG. 3). Such cell-type specificity is not uncommon. In addition, B3CD induced apoptosis; distinct DNA laddering characteristic of apoptosis was observed in neuroblastic, ovarian and prostate cancer cells. However, keratinocytes were not affected by B3CD (FIG. 4A; Lane-2). In addition, caspase-3 activity was increased by B3CD (FIG. 4B). These studies indicated an underlying apoptotic mechanism in the anticancer activity of B3CD. B3CD induced rapid apoptosis in neuroblstic cells and cell viability was less than 15% of the untreated control cells by 24 hours.

Figure 5:
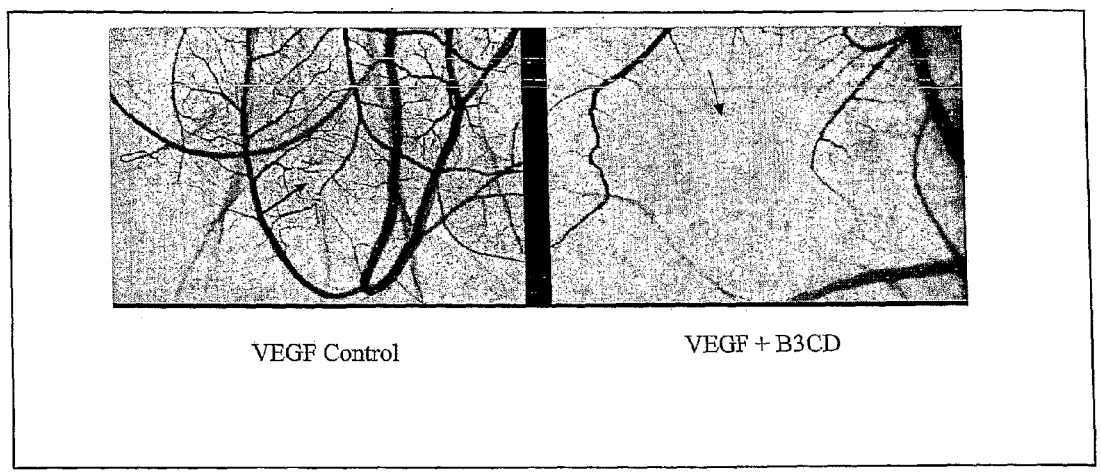
FIG. 5. CAM assay for angiogenesis compared with B3CD inhibited VEGF induced angiogenesis.

The antiproliferative effect of B3CD on endothelial cells was further investigated. B3CD induced apoptosis in endothelial cells (data not shown). When tested for its effect on angiogenesis, B3CD inhibited VEGF induced angiogenesis in chick chorioallantoic membrane (CAM) assay (FIG. 5). There was a dense network of fine capillary visible around the treatment area in VEGF control eggs, which was markedly reduced in the case of B3CD treated eggs. Close examination of the CAMs of treated eggs revealed that B3CD inhibited neovascularization by ~60% when compared to untreated controls suggesting that B3CD is a potent inhibitor of angiogenesis.

Neuroblastoma cells were treated with B3CD for 48 hrs. B3CD inhibited the proliferation SK-N-SH, SH-Sy5Y, SMS-KCN and SMS-R neuroblastic cells in a dose dependent manner. AT 0.5 nM, B3CD inhibited >50% (p<0.035) and >90% at 1.0M (p<0.01) viability and proliferation respectively. B3CD activated caspase-3 and induced apoptosis. It inhibited phosphorylation of ERK1/2 and AKT demonstrating the role of MAPK and AKT pathways. B3CD also inhibited TrkB signaling by BDNF indicating that B3CD suppresses BDNF mediated chemoprotection generally observed in neuroblastoma.

Example 4

In Vivo Studies to Assess Systemic Toxicity

Figure 1:
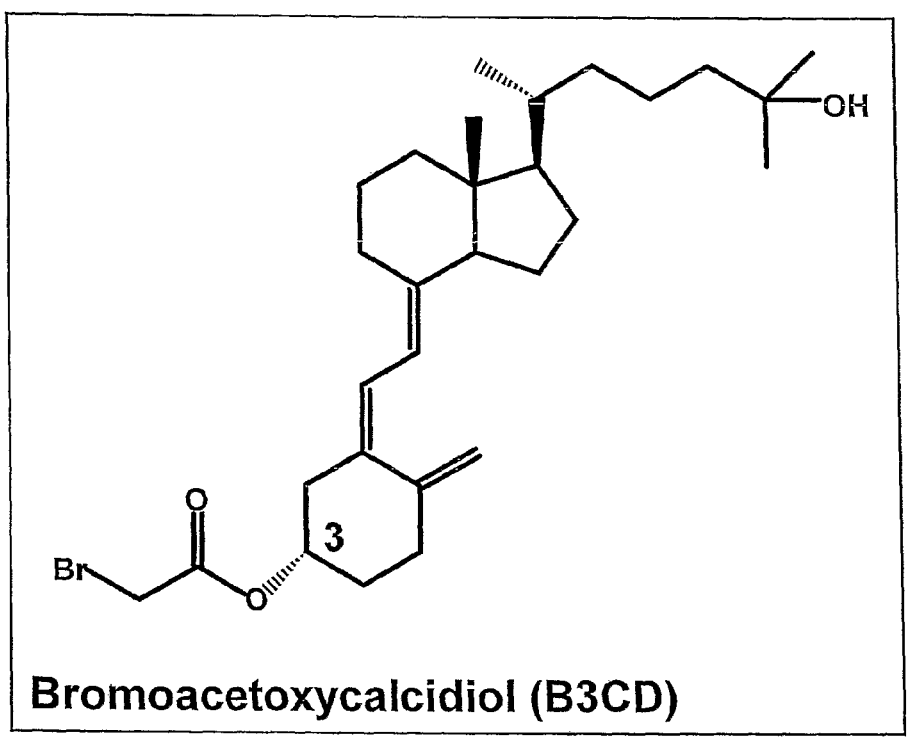
FIG. 1. Chemical structure of B3CD.
Figure 6:
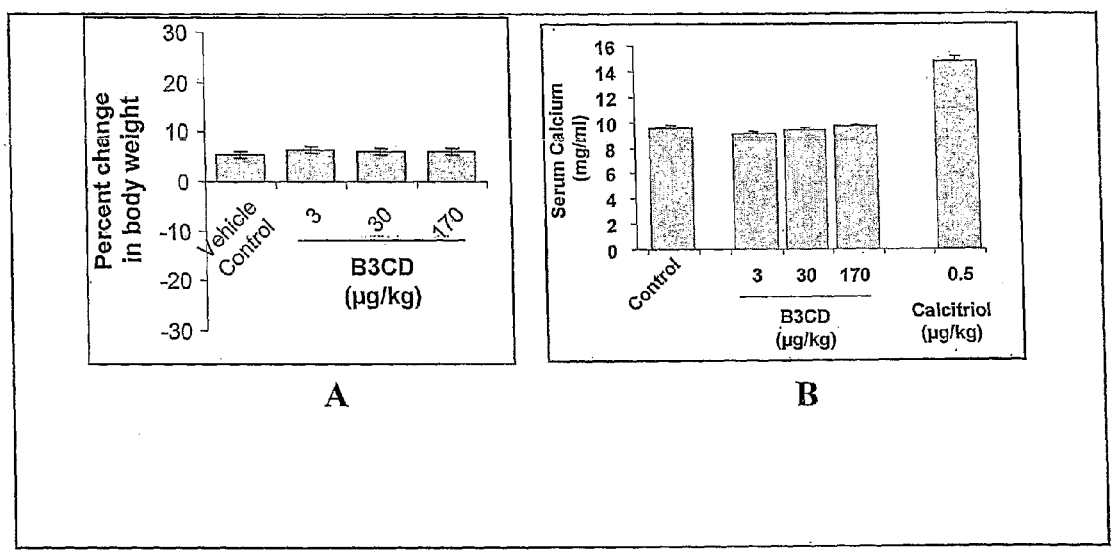
FIG. 6A. In vivo studies to determine apparent systemic toxicity of B3CD. Mice were injected with the specified amounts of B3CD (i.p.) once in 48 hr for 28 days. The animals were weighed to assess the effect of B3CD on change in body weight.
FIG. 6B. At the end of the experiment (6A) mice were sacrificed and blood collected to estimate serum calcium as a measure of hypercalcemia.

A major concern was the potential systemic toxicity of B3CD due to hypercalcemia since B3CD (FIG. 1) is a derivative of calcidiol, which is a family member of calcitriol (Schmidt-Gayk H, Bouillon R, Roth H J. Measurement of vitamin D and its metabolites (calcidiol and calcitriol) and their clinical significance. *Scand J Clin Lab Invest Suppl.* 1997; 227:35-45). Therapeutic doses of calcitriol lead to increased serum calcium and consequently death; therefore, hypercalcemia is a hallmark of lethality of pharmacologic doses of calcitriol. In the event that further testing in vivo might show lethal calcemic side effects, preliminary studies were carried out to determine any overt toxic effects in a murine model. Administration of B3CD to mice did not cause elevation of serum calcium level or loss of body weight, indicating a lack of general systemic toxicity (FIG. 6A-B).

In the above experiments, calcidiol, the parent compound was used as a control; however, it did not exhibit any antiproliferative, cytotoxic, apoptotic activities or hypercalcemia (data not shown).

Based on these observations, B3CD was identified as a potential chemotherapeutic compound, which can be used as a lead compound to develop novel therapeutic molecules centered on the B3CD scaffold. The molecular determinants responsible for cytotoxic action of B3CD can be assessed and each of the newly synthesized compounds characterized for antiproliferative, cytotoxic and apoptogenic activities and compared with B3CD, which was shown to inhibit proliferation of endothelial cells and angiogenesis in CAM assay. Administration of B3CD to mice did not cause hypercalcemia or weight loss, indicating lack of apparent toxicity

Example 5

Synthesis of B3CD

An earlier reported synthesis with suitable modifications was used to synthesize B3CD. Briefly, equimolar amounts of calcidiol and bromoacetic acid were stirred with excess of dicyclohexylcarbodiimide and dry pryridine in dichloromethane in ice bath for 2-4 hours. The product, B3CD was isolated using preparative TLC and HPLC, and characterized by NMR and mass-spectrometry.

Example 6

B3CD Inhibits Proliferation of Neuroblastic Cells

Figure 7:
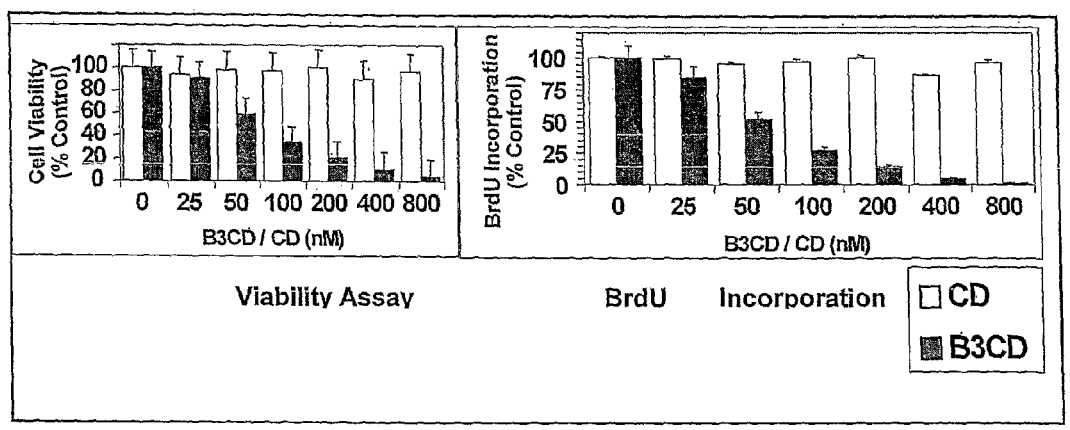
FIG. 7. Inhibition of SKNSH proliferation by B3CD.

SK-N-SH and SH-SY5Y neuroblastic cells were treated with increasing doses of calcidiol or B3CD (0, 25, 50, 100, 200, 400 and 800 nM) for 48 hours. Cell viability was assessed by MTS assay and proliferation was determined by BrdU incorporation assay. There was a dose dependent decrease in viability and proliferation of both SK-N-SH cells following treatment with B3CD (FIG. 7). B3CD reduced the viability of SK-N-SH cells significantly (less than 20% of the untreated control at a dose level of 200 nM), while treatment with CD did not show any similar effects. There was a strong inhibition of proliferation as indicated by diminished BrdU incorporation. On the other hand, the parent compound, calcidiol did not show inhibitory activity on these cells. Similar dose dependent inhibition of viability and proliferation was observed in SH-SY5Y cells treated with B3CD (data not shown). These studies showed that B3CD is a potent inhibitor of proliferation of neuroblastic cells.

Example 7

B3CD is a Potent Inducer of Apoptosis in NB Cells

Initially, during regular microscopic examination of the B3CD treated cells, the cells were condensing and floating in the culture dishes showing indications of apoptosis. In order to determine apoptosis, SK-N-SH and SH-SY5Y cells were treated with 250 nM B3CD for 48 hours. DNA was isolated and analyzed by agarose gel electrophoresis. A distinct DNA laddering pattern characteristic of apoptosis was observed in B3CD treated SK-N-SH and SH-SY5Y cells (FIG. 8) indicating that B3CD is a potent inducer of apoptosis in NB cells.

Example 8

Cell Cycle

Cell cycle analysis of 400 nm B3CD treated SK-N-SH cells showed a G0/G1 block, inhibition of S-phase and increased apoptotic cells (from 7% in control to 45% in B3CD treated cells) further indicating a role of apoptosis (data not shown).

Caspases are integral to apoptosis in cells. Following the treatment of SK-N-SH cells with 250 nM B3CD, activation of caspase-3 was measured by using specific substrate. Caspase-3 activity was increased by ~6 fold upon treatment with B3CD when compared to vehicle treated control (FIG. 9); furthermore, calcidiol did not show any significant change in the caspase-3 activation. Similar caspase-3 activation was observed in SH-SY5Y cells. Together these studies clearly showed that B3CD induced apoptosis in NB cells.

Example 9

B3CD Effect on NB Cells Defective in Apoptotic Pathways

NB is characterized with defective apoptotic pathways. Since B3CD induced apoptosis in SK-N-SH NB cells, the ability B3CD to induce apoptosis in NB cells with well documented defects in apoptosis pathways was tested. Neuronal (N-) type SH-SY5Y and IMR-32 cells, and stromal (S-) type SMS-KCNR cells which are resistant to apoptosis were used. SMS-KCNR cells have been shown to express caspase-8 while, SH-SY5Y and IMR-32 have no detectable caspase-8 expression; caspase-8 activation is integral to extrinsic pathway of apoptosis. A defect in caspase-8 or its activation causes resistance to apoptosis and in turn to chemotherapy in all these cells. On the other hand, these cells carry intact intrinsic apoptotic pathway, and executioner caspase-3 is activated by caspase-9 route. Despite defects in caspase-8 activation, these cells undergo apoptosis and activation of caspase-9 and -3 when treated with doxorubicin.

Treatment of IMR-32 and SMS-KCNR cells with B3CD resulted in a dose dependent inhibition of proliferation similar to SH-SY5Y, SK-N-SH cells and induced apoptosis (data not shown). In depth studies were carried out to assess the activation of intrinsic and extrinsic apoptotic pathways. The results are shown in FIG. 10. B3CD activated caspase-3 in SMS-KCNR, IMR-32 and SH-SY5Y cells (FIG. 10A).

Caspase-9 was activated by B3CD in these cells (FIG. 10B), indicating an active role of intrinsic pathway of apoptosis. In addition, cytochrome-c (which is integral to caspase-9 activation) is released into cytosol upon treatment with B3CD (FIG. 10C), which further supports the involvement of intrinsic pathway in inducing apoptosis. However, caspase-8 was undetectable in IMR-32 and SH-SY5Y cells.

Although caspase-8 was detected in SMS-KCNR cells, it was not activated by B3CD (FIG. 10D). Actin immunoblotting was used as loading control in the above studies (data not shown). Additionally, pretreatment of IMR-32 and SMS-KCNR cells with caspase-9 inhibitor, Z-LEHD-FMK effectively inhibited apoptosis (FIG. 11) clearly indicating that B3CD induced apoptosis via intrinsic pathway in these cells. These observations suggest that B3CD may be inducing apoptosis via the activation of intrinsic pathway while circumventing the caspase-8 mediated extrinsic pathway, which is often defective in NB.

Example 10

Anti-Angiogenic Properties of B3CD

B3CD inhibited proliferation of endothelial cells (EC). Angiogenesis is the biological process by which new capillaries are formed from pre-existing vessels. Excessive angiogenesis occurs in solid tumor growth and has been shown to be an integral part of pathology of NB.

Human umbilical vein endothelial cells (HUVEC) were treated with B3CD (25, 50, 100, 200 and 400 nM) for 24 hours and proliferation was measured as before. Vehicle and CD treated controls were used in each experiment. B3CD strongly inhibited the proliferation of EC as shown in FIG. 12. There was a dose dependent decrease in viability of EC upon treatment with B3CD (FIG. 12A). B3CD strongly inhibited BrdU incorporation also (FIG. 12B). The effect of B3CD on proliferation of EC was comparable to that of on NB and other cancer cells tested. Proliferation inhibition studies showed that B3CD is potent inhibitor of EC proliferation. Following the treatment with B3CD, the endothelial cells were rounded up and floated, showing indications of apoptosis similar to NB.

Example 11

B3CD Induces Apoptosis in Endothelial Cells

Similar to neuroblastic cells, upon treatment with B3CD, EC also showed signs of apoptosis. Apoptosis in EC by B3CD was studied by DNA fragmentation and caspase-3 activation analyses as before. B3CD treatment resulted in DNA fragmentation characteristic of apoptosis as shown in FIG. 13 indicating apoptosis. There was a 5-fold increase in caspase-3 activity upon treatment with B3CD suggesting a role of caspase-3 in apoptosis of EC (data not shown). These studies clearly indicated that B3CD induces apoptosis in endothelial cells similar to neuroblastic cells.

Example 12

B3CD Inhibits Angiogenesis

The ability of B3CD to inhibit angiogenesis/neovascularization was tested. Preliminary studies were carried out using chick chorioallantoic membrane (CAM) assay. Calcidiol or B3CD were deposited in the presence of growth factor (VEGF) and deposited on the CAM and eggs were incubated for 3 days at 37° C. (3% $CO_2$). The control carried the growth factor alone. VEGF induces angiogenesis which results in sprouting of capillaries from the large vessels. The compounds diffuse out and any inhibitory molecule would reduce the growth of blood vessel network. There was a dense network of fine capillary visible around the treatment area in control eggs (small arrows, FIG. 14); where as the density of fine capillary network was markedly reduced the in case of B3CD treated eggs. FIG. 14 shows representative photographs from the CAM assay. Close examination of the CAMs of treated eggs revealed that B3CD inhibited neovascularization by ~60% when compared to untreated controls. There was no inhibition of neovascularization by calcidiol (data not shown), CAM assay suggested that B3CD inhibits angiogenesis.

Example 13

In Vivo Studies

A major concern in testing B3CD as an anticancer agent in vivo was the potential systemic toxicity of B3CD due to hypercalcemia since, B3CD is a derivative of calcidiol, a family member of calcitriol. Therapeutic doses of calcitriol lead to increased calcium level in blood. Although B3CD is a derivative of calcidiol, and not calcitriol, further testing of B3CD in vivo could show that B3CD may have acquired the lethal calcemic side effects of calcitriol. Therefore, it was important to determine the effect of B3CD on serum calcium levels (calcemic activity) in vivo in order to establish its therapeutic potential.

The effect of B3CD on serum calcium levels in SCID mice was tested. These studies were carried out in Boston University School of Medicine, Boston, Mass., in accordance with institutional guidelines. B3CD, calcidiol and calcitriol were formulated in 80% polyethylene glycol in PBS and were administered as i.p. injections once in 48 hours for 28 days. Animals were euthanized, sera collected and analyzed immediately for serum calcium in the hospital core facility. The animals were divided into 4 groups of 5 animals each.

Compared with their initial weights, the mean weight of mice in the control group increased by 5.4% during the 28 days of the experiment. There was a drastic loss of body weight in calcitriol treated group; the mice lost about 25% (P<0.001 compared to control) of their body weight indicating the toxicity of calcitriol. However, there was no loss in the body weight in B3CD or CD treated groups (P<0.04 and 0.035 respectively when compared to control group) and increase was similar to that of control (FIG. 15A). Calcitriol-treated animals appeared lethargic and exhibited a decreased tolerance to handling with reduced mobility. Conversely, rats treated with B3CD showed no such signs. These studies indicated lack of lethal side effects of B3CD.

Serum calcium levels are an important measure of toxicity of calcitriol-based compounds. Mice treated with B3CD or CD did not show any change in the serum calcium levels when compared to control group. Compared to the serum calcium levels of 9.23±0.15 mg/ml, mean serum concentrations of B3CD treated group was 9.1±0.2, 9.4±0.2 and 9.7±0.1 mg/ml for 3, 30 and 170 µg/ml. Similar to B3CD, CD treated animals also did not show any change in serum calcium levels (FIG. 15B). However, calcitriol showed a drastic increase in serum calcium levels, (14.65±0.23 mg/ml) indicating hypercalcemia. This correlated well with the severe loss of body weight. Together these studies demonstrated a lack of apparent toxicity of B3CD in vivo and feasibility of testing B3CD in animal models of neuroblastoma.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

All publications, patent applications, patents, and other documents cited herein are incorporated by reference in their entirety. In case of conflict, the present specification, including definitions, will control. In addition, the materials, methods, and examples are illustrative only and not intended to be limiting.

What is claimed is:

1. The compound 6-(2,4-Dinitro-phenylamino)-hexanoic acid 2-(4-(2-bromo-acetoxy-2-{2-[1-(5-hydroxy-1,5-dimethyl-hexyl)-7a-methyl-octahydro-inden-4-ylidene]-ethylidene}-cyclohexylidene)-ethyl ester

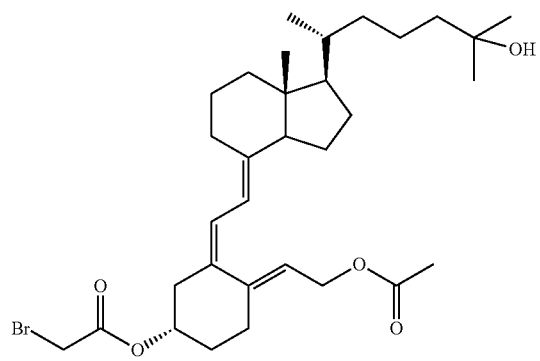

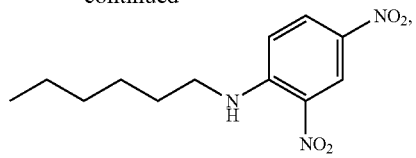

or a pharmaceutically acceptable salt, solvate, clathrate, stereoisomer, enantiomer or prodrug thereof.

2. A pharmaceutical composition comprising the compound of claim 1 and a pharmaceutically acceptable carrier.

3. A packaged formulation for use in inhibiting cancer cell proliferation, wherein the cancer cell is selected from the group consisting of colon, ovarian, prostate, neuroblastoma and acute promyelocytic leukemia, comprising a pharmaceutical composition comprising the compound of claim 1 and instructions for use in a method for inhibiting said cancer cell proliferation.

4. A method for inhibiting cancer cell proliferation, wherein the cancer cell is selected from the group consisting of colon, ovarian, prostate, neuroblastoma and acute promyelocytic leukemia, comprising administering to said cell an amount of the compound of claim 1 effective to inhibit proliferation of the said cancer cell.

5. The method of claim 4, wherein the cancer cell is a neuroblastoma cell.

6. The method of claim 5, wherein the neuroblastoma cell is selected from the group consisting of SK-N-SH, SH-SY5Y, SMS-KCN and SMS-KCNR.

7. The method of claim 4, wherein the cancer cell is a prostate cancer cell.

8. The method of claim 4, wherein the cancer cell is an endothelial cell.

9. The method of claim 4, wherein the cancer cell is comprised within a mammal.

10. The method of claim 8, wherein the mammal is human.

* * * * *